(12) United States Patent
Huddleston et al.

(10) Patent No.: US 11,648,114 B2
(45) Date of Patent: May 16, 2023

(54) DISTALLY LOADED SHEATH AND LOADING FUNNEL

(71) Applicant: Tendyne Holdings, Inc., St. Paul, MN (US)

(72) Inventors: Preston James Huddleston, Maplewood, MN (US); Mitchell F. McBride, Minneapolis, MN (US); Nathan T. Smith, Shoreview, MN (US); Aaron L. Swandal, Savage, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 167 days.

(21) Appl. No.: 17/123,403

(22) Filed: Dec. 16, 2020

(65) Prior Publication Data
US 2021/0186695 A1    Jun. 24, 2021

Related U.S. Application Data

(60) Provisional application No. 62/951,434, filed on Dec. 20, 2019.

(51) Int. Cl.
*A61F 2/24*   (2006.01)
*A61F 2/95*   (2013.01)

(52) U.S. Cl.
CPC .......... *A61F 2/2433* (2013.01); *A61F 2/2436* (2013.01); *A61F 2/9525* (2020.05); *A61F 2002/9505* (2013.01)

(58) Field of Classification Search
CPC .... A61F 2/2433; A61F 2/2436; A61F 2/9525; A61F 2002/9505; A61F 2/9517; A61F 2/2418; A61F 2/2457
See application file for complete search history.

(56) References Cited

U.S. PATENT DOCUMENTS

| 2,697,008 A | 12/1954 | Ross |
| 3,409,013 A | 11/1968 | Berry |
| (Continued) | | |

FOREIGN PATENT DOCUMENTS

| AU | 2002212418 B2 | 3/2006 |
| CN | 1486161 A | 3/2004 |
| (Continued) | | |

OTHER PUBLICATIONS

US 9,155,620 B2, 10/2015, Gross et al. (withdrawn)
(Continued)

*Primary Examiner* — Shaun L David
*Assistant Examiner* — Rachael L Geiger
(74) *Attorney, Agent, or Firm* — Wei & Sleman LLP

(57) ABSTRACT

A heart valve delivery system may include a handle, a shaft having a proximal end fixedly connected to the handle and extending distally along an axis away from the handle to a free end, and a tube surrounding the shaft. The tube may have a proximal end connected to the handle and extend distally along the axis away from the handle to a distal end. The tube may be axially movable relative to the shaft and the handle between a fully extended position at which the tube extends distally farther than the shaft, and a fully retracted position at which the shaft extends distally farther than the tube. The system may include an inserter for guiding insertion of the tube. In addition or in alternative to the inserter, the system may include a funnel for loading the prosthetic valve into the tube.

20 Claims, 18 Drawing Sheets

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |

(56) References Cited

U.S. PATENT DOCUMENTS

| | | |
|---|---|---|
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,716 B1 * | 12/2003 | Gilson ............ A61F 2/95 606/198 |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |

(56) References Cited

U.S. PATENT DOCUMENTS

| | | |
|---|---|---|
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,579,963 B2 | 11/2013 | Tabor |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,364,325 B2 | 6/2016 | Alon et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 11,191,642 B2 * | 12/2021 | Haynes ................ A61F 2/2436 |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0055606 A1 | 3/2004 | Hendricksen et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0096735 A1 | 5/2005 | Hojeibane et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288763 A1 | 12/2005 | Andreas et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |

(56) References Cited

U.S. PATENT DOCUMENTS

| | | |
|---|---|---|
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2006/0287719 A1 | 12/2006 | Rowe et al. |
| 2007/0005131 A1 | 1/2007 | Taylor |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0088431 A1 | 4/2007 | Bourang et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0054976 A1 | 2/2009 | Tuval et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0234940 A1 | 9/2010 | Dolan |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |

(56) References Cited

U.S. PATENT DOCUMENTS

| | | |
|---|---|---|
| 2010/0298755 A1 | 11/2010 | McNamara et al. |
| 2010/0298931 A1* | 11/2010 | Quadri .................. A61F 2/95 623/2.11 |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029071 A1 | 2/2011 | Zlotnick et al. |
| 2011/0029072 A1 | 2/2011 | Gabbay |
| 2011/0046712 A1 | 2/2011 | Melsheimer et al. |
| 2011/0054519 A1 | 3/2011 | Neuss |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0218619 A1 | 9/2011 | Benichou et al. |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1* | 10/2011 | Rothstein ............ A61F 2/2436 623/1.11 |
| 2011/0264206 A1 | 10/2011 | Tabor |
| 2011/0288637 A1 | 11/2011 | De Marchena |
| 2011/0301703 A1 | 12/2011 | Glazier |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0078347 A1 | 3/2012 | Braido et al. |
| 2012/0083874 A1 | 4/2012 | Dale et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0239142 A1 | 9/2012 | Liu et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0059747 A1 | 3/2013 | Mann et al. |
| 2013/0066341 A1 | 3/2013 | Ketai et al. |
| 2013/0079873 A1 | 3/2013 | Migliazza et al. |
| 2013/0090728 A1 | 4/2013 | Solem |
| 2013/0116772 A1* | 5/2013 | Robinson .............. A61F 2/966 623/1.12 |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0268064 A1 | 10/2013 | Duffy |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0005767 A1 | 1/2014 | Glazier et al. |
| 2014/0046433 A1 | 2/2014 | Kovalsky |
| 2014/0081323 A1 | 3/2014 | Hawkins |
| 2014/0088695 A1 | 3/2014 | Figulla et al. |
| 2014/0094918 A1 | 4/2014 | Vishnubholta et al. |
| 2014/0128963 A1 | 5/2014 | Quill et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0316518 A1 | 10/2014 | Kheradvar et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson et al. |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305867 A1 | 10/2015 | Liu et al. |
| 2015/0305868 A1 | 10/2015 | Lutter et al. |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |

(56) References Cited

U.S. PATENT DOCUMENTS

| | | | |
|---|---|---|---|
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1* | 2/2018 | Ekvall .................. A61F 2/2436 |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |
| 2018/0263618 A1 | 9/2018 | Vidlund et al. |
| 2019/0117394 A1* | 4/2019 | Morin .................. A61F 2/2427 |

FOREIGN PATENT DOCUMENTS

| | | |
|---|---|---|
| CN | 1961845 A | 5/2007 |
| CN | 2902226 Y | 5/2007 |
| CN | 101146484 A | 3/2008 |
| CN | 101180010 A | 5/2008 |
| CN | 101984938 A | 3/2011 |
| CN | 102869317 A | 1/2013 |
| CN | 102869318 A | 1/2013 |
| CN | 102869321 A | 1/2013 |
| CN | 103220993 A | 7/2013 |
| CN | 102639179 B | 10/2014 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2007509700 A | 4/2007 |
| JP | 2008504078 A | 2/2008 |
| JP | 2008541863 A | 11/2008 |
| JP | 2009511229 A | 3/2009 |
| JP | 2009514628 A | 4/2009 |
| JP | 2009519783 A | 5/2009 |
| JP | 2012504031 A | 2/2012 |
| JP | 2012518465 A | 8/2012 |
| JP | 2012519024 A | 8/2012 |
| JP | 2013512765 A | 4/2013 |
| JP | 2013525039 A | 6/2013 |
| JP | 2013538086 A | 10/2013 |
| JP | 2014513585 A | 6/2014 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 200041652 A1 | 7/2000 |
| WO | 200047139 A1 | 8/2000 |
| WO | 2001035878 A2 | 5/2001 |
| WO | 0149213 A2 | 7/2001 |
| WO | 200149213 A3 | 7/2001 |
| WO | 0154625 A1 | 8/2001 |
| WO | 2001054624 A1 | 8/2001 |
| WO | 2001056512 A1 | 8/2001 |
| WO | 2001061289 A1 | 8/2001 |
| WO | 200176510 A2 | 10/2001 |
| WO | 2001082840 A1 | 11/2001 |
| WO | 2002004757 A1 | 1/2002 |
| WO | 2002022054 A1 | 3/2002 |
| WO | 2002028321 A2 | 4/2002 |
| WO | 0236048 A1 | 5/2002 |
| WO | 2002036048 A1 | 5/2002 |
| WO | 2002041789 A2 | 5/2002 |
| WO | 2002043620 A1 | 6/2002 |
| WO | 2002049540 A2 | 6/2002 |
| WO | 02076348 A1 | 10/2002 |
| WO | 2003003943 A2 | 1/2003 |
| WO | 2003030776 A2 | 4/2003 |
| WO | 2003047468 A1 | 6/2003 |
| WO | 2003049619 A2 | 6/2003 |
| WO | 03063740 A1 | 8/2003 |
| WO | 2004019825 A1 | 3/2004 |
| WO | 2005102181 A1 | 11/2005 |
| WO | 2006005082 A2 | 1/2006 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009094500 A1 | 7/2009 |
| WO | 2009132187 A1 | 10/2009 |
| WO | 2010022138 A2 | 2/2010 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |

(56) References Cited

FOREIGN PATENT DOCUMENTS

| WO | 2012177942 A2 | 12/2012 |
|---|---|---|
| WO | 2013028387 A2 | 2/2013 |
| WO | 2013045262 A1 | 4/2013 |
| WO | 2013059747 A1 | 4/2013 |
| WO | 2013096411 A1 | 6/2013 |
| WO | 2013175468 A2 | 11/2013 |
| WO | 2014071077 A1 | 5/2014 |
| WO | 2014121280 A2 | 8/2014 |
| WO | 2014144937 A2 | 9/2014 |
| WO | 2014162306 A2 | 10/2014 |
| WO | 2014189974 A1 | 11/2014 |
| WO | 2014210124 A1 | 12/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

International Search Report and Written Opinion for International Application No. PCT/US2014/040188, dated Nov. 17, 2014, 12 pages.

Invitation to Pay Additional Fees and Partial International Search Report for International Application No. PCT/US2014/040188, dated Sep. 8, 2014, 5 pages.

Office Action for Chinese Application No. 201480037269.5, dated Dec. 23, 2016.

L. L. Knudsen et al., "Catheter-Implanted Prosthetic Heart Valves. Transluminal Catheter Implantation of a New Expandable Artificial Heart Valve in the Descending Thoracic Aorta in Isolated Vessels and Closed Chest Pigs," International Journal of Artificial Organs, 1993, Issue 5, vol. 16, pp. 253-262.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Examination Report No. 1 for Australian Application No. 2014274056, dated Mar. 6, 2018, 4 pages.

Examination Report No. 2 for Australian Application No. 2014274056, dated May 9, 2018, 4 pages.

Second Office Action for Chinese Application No. 201480037269.5, dated Nov. 6, 2017, 6 pages.

Third Office Action for Chinese Application No. 201480037269.5, dated Jun. 19, 2018, 8 pages.

Examination Report for European Application No. 14734333.9, dated Oct. 20, 2016, 6 pages.

Notice of Reasons for Rejection for Japanese Application No. 2016-517032, dated Feb. 13, 2018, 5 pages.

Extended European Search Report for European Application No. 18160595.7, dated Sep. 14, 2018, 7 pages.

Office Action for U.S. Appl. No. 14/950,656, dated Apr. 22, 2016, 5 pages.

Japanese Office Action for Application No. 2020105100, dated Jun. 4, 2021, 4 pages.

Al Zaibag, Muayed, et al., "Percutaneous Balloon Valvotomy in Tricuspid Stenos's," British Heart Journal, Jan. 1987, vol. 57, No. 1, pp. 51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.

Andersen, H. R., "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2):102-106.

Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.

Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.

Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration In Dilated Hearts," Interactive Cardiovascular and Thoracic Surgery, 2005, 4:475-477.

Chamberlain, G., "Ceramics Replace Body Parts," Design News, Jun. 9, 1997, Issue 11, vol. 52, 5 pages.

Choo, S. J. et al., "Aortic Root Geometry: Pattern of Differences Between Leaflets and Sinuses of Valsava," The Journal of Heart Valve Disease, Jul. 1999, 8:407-415.

Declaration of Malcolm J. R. Dalrymple-Hay, Nov. 9, 2012, pp. 1-11; with Curriculum Vitae, Oct. 4, 2012.

Dotter, C. T. et al., "Transluminal Treatment of Arteriosclerotic Obstruction. Description of a New Technic and a Preliminary Report of its Application," Circulation, Nov. 1964, 30:654-670.

Drawbaugh, K., "Feature—Heart Surgeons Explore Minimally Invasive Methods," Reuters Limited, Jul. 16, 1996, 3 pages.

Gray, H., The Aorta, Anatomy of the Human Body, 1918, Retrieved from the Internet <http://www.bartleby.com/107/142. html>, Oct. 12, 2012, 5 pages.

Gray, H., The Heart, Anatomy of the Human Body, 1918, Retrieved from the Internet <http://education.yahoo.com/reference/gray/subjects/subject/138>, Oct. 8, 2012, 9 pages.

Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.

Inoue, K. et al., "Clinical Application of Transvenous Mitral Commissurotomy by a New Balloon Catheter," The Journal of Thoracic and Cardiovascular Surgery, 1984, 87:394-402.

Jin, X. Y. et al., "Aortic Root Geometry and Stentless Porcine Valve Competence," Seminars in Thoracic and Cardiovascular Surgery, Oct. 1999, 11(4):145-150.

Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.

Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

(56) References Cited

OTHER PUBLICATIONS

Lutter, Georg, et al., Mitral valved stent implantation, European Journal of Cardio-Thoracic Surgery, 2010, vol. 38, pp. 350-355.
Ma, L. et al., "Double-crowned valved stents for off-pump mitral valve replacement," European Journal of Cardio-Thoracic Surgery, Aug. 2005, 28(2): 194-198.
Moazami, N. et al., "Transluminal aortic valve placement: A feasibility study with a newly designed collapsible aortic valve," ASAIO Journal, Sep./ Oct. 1996, 42(5):M381-M385.
Orton, C., "Mitralseal: Hybrid Transcatheter Mitral Valve Replacement," Symposium: Small Animal Proceedings, 2011, pp. 311-312.
Pavcnik, D. et al. "Development and Initial Experimental Evaluation of a Prosthetic Aortic Valve for Transcatheter Placement," Radiology, 1992; 183:151-154.
Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.
Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.
Rosch, J. et al., "The Birth, Early Years and Future of Interventional Radiology," J Vasc Interv Radiol., Jul. 2003, 4:841-853.
Ross, D. N., "Aortic Valve Surgery," Guy's Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart Valves," In Polymetric Materials and Artificial Organs, Mar. 20, 1983, pp. 111-150, American Chemical Society.
"Shape Memory Alloys," Retrieved from the Internet: <http://webdocs.cs.ualberta.ca/~database/MEMS/sma.html>, Feb. 5, 2016, 3 pages.
Extended European Search Report including Written Opinion for Application No. EP20168419.8, dated Jul. 21, 2020, pp. 1-8.
US 9,155,620, 10/2015, Gross et al. (withdrawn)

\* cited by examiner

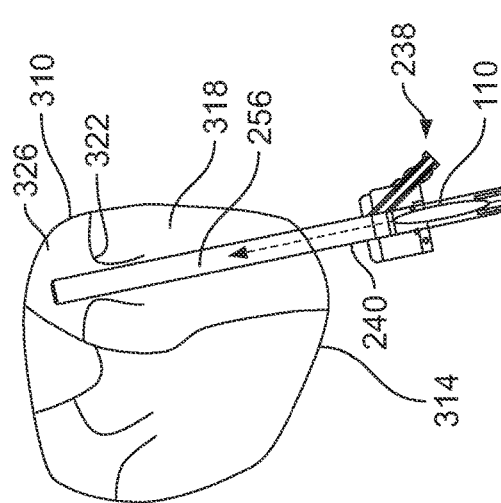
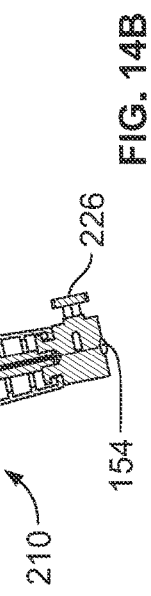
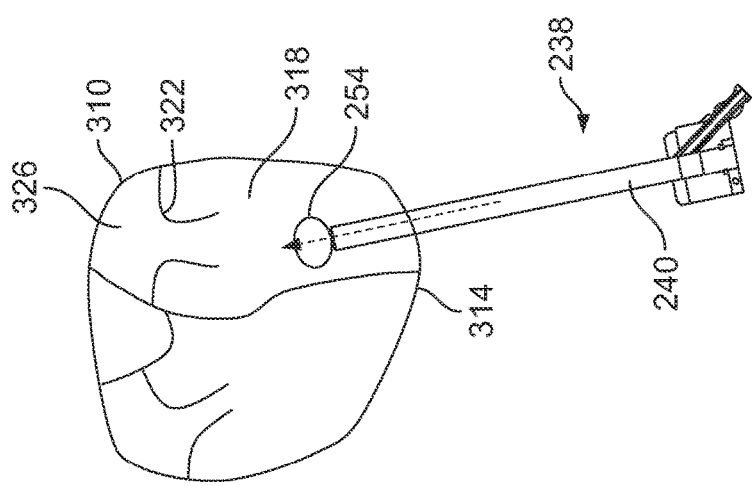
FIG. 14B
FIG. 14A

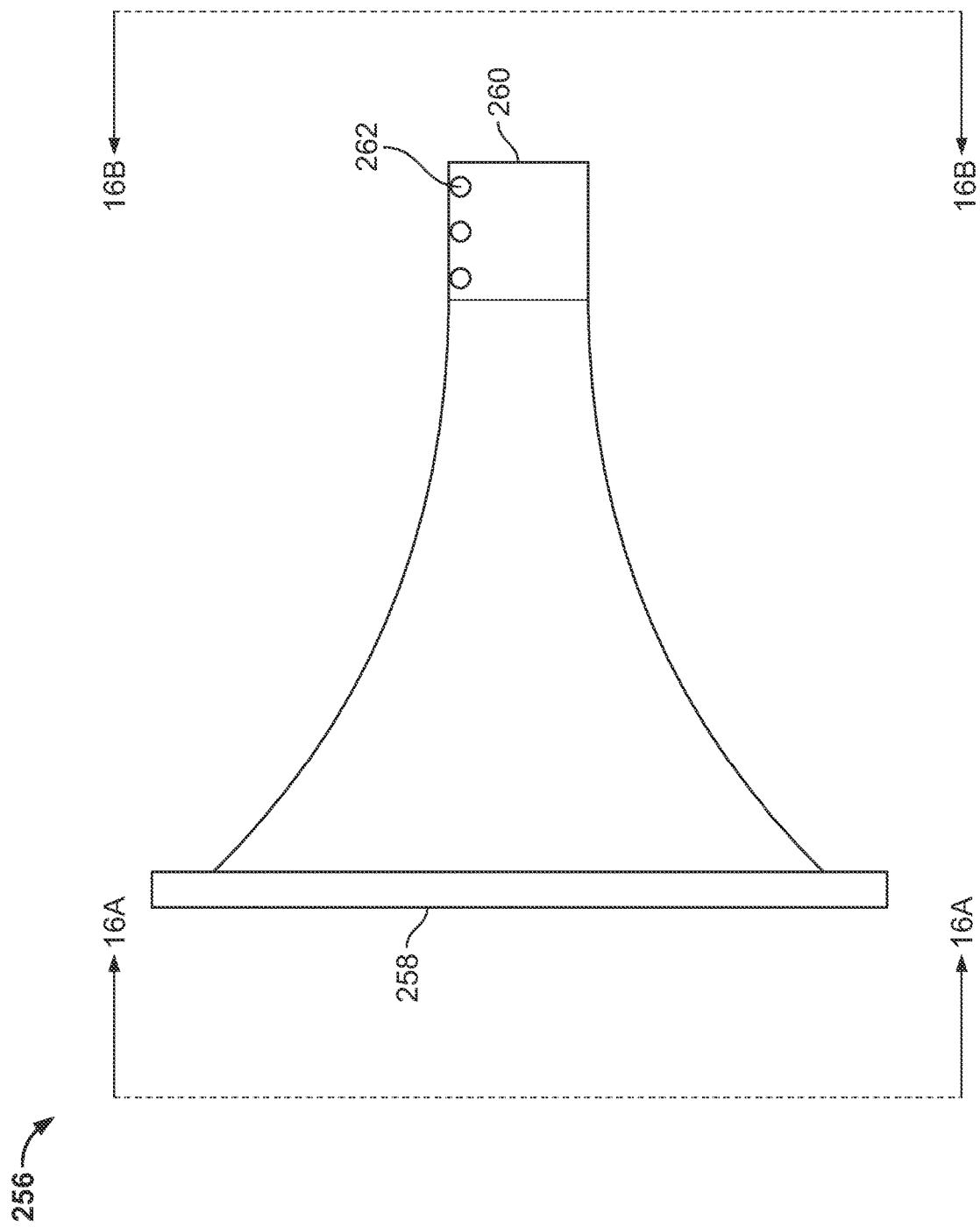

DISTALLY LOADED SHEATH AND LOADING FUNNEL

CROSS-REFERENCE TO RELATED APPLICATIONS

The present application claims the benefit of the filing date of U.S. Provisional Patent Application No. 62/951,434 filed Dec. 20, 2019, the disclosure of which is hereby incorporated by reference.

BACKGROUND

Valvular heart disease, and specifically aortic and mitral valve disease, is a significant health issue in the United States. Annually, approximately 90,000 valve replacements are performed in the United States. Traditional valve replacement surgery, the orthotopic replacement of a heart valve, is an "open heart" surgical procedure. Briefly, the procedure necessitates a surgical opening of the thorax, initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated with the procedure, largely due to the necessity for extra-corporeal circulation. Further, open heart surgery is often poorly tolerated in elderly patients. Thus, if the extra-corporeal component of the procedure could be eliminated, morbidities and cost of valve replacement therapies would be significantly reduced.

While replacement of the aortic valve in a transcatheter manner is the subject of intense investigation, lesser attention has been focused on the mitral valve. This is in part reflective of the greater level of complexity associated with the native mitral valve and thus a greater level of difficulty with regard to inserting and anchoring the replacement prosthesis.

Recent developments in the field have provided devices and methods for mitral valve replacement with reduced invasion and risk to the patient. However, due to factors including the need to maintain hemostatic pressure and avoid air embolism, such devices have complex designs and require time, space, and labor intensive loading procedures. Accordingly, there is a need for simplified devices and methods for loading and delivering replacement heart valves, particularly replacement mitral valves.

BRIEF SUMMARY

In some arrangements, a heart valve delivery system may include a handle, a shaft having a proximal end fixedly connected to the handle and extending distally along an axis away from the handle to a free end, and a tube surrounding the shaft. The tube may have a proximal end connected to the handle and extend distally along the axis away from the handle to a distal end. The tube may be axially movable relative to the shaft and the handle between a fully extended position at which the tube extends distally farther than the shaft, and a fully retracted position at which the shaft extends distally farther than the tube.

In further arrangements, a heart valve delivery system may include a handle, a tube, a distal nose, an inserter, and/or a funnel. The handle may have a longitudinally extending slot, a cavity, an annular adjustor with interior threading, and a pin block bounding an end of the cavity, the pin block including a bore and a set screw extending into the bore. The shaft may have a proximal end fixedly connected to the handle and extending distally along an axis away from the handle to a free end. The shaft may further have a shaft lumen extending from the proximal end to the distal end, and a retainer located at the free end and including an interior space in communication with the shaft lumen. The tube may surround the shaft, the tube having a proximal end connected to the handle and extending distally along the axis away from the handle to a distal end and having a tube lumen extending from the proximal end of the tube to the distal end of the tube, the tube being axially movable relative to the shaft and the handle between a fully extended position at which the tube extends distally farther than the shaft, and a fully retracted position at which the shaft extends distally farther than the tube. The distal nose may be fixedly connected to the proximal end of the tube. The inserter may have a tubular sheath with an inner diameter greater than an outer diameter of the tube. The inserter may be releasably couplable to the distal nose to restrain axial movement of the inserter relative to the tube. The funnel may include a first portion having an inner diameter equal to an inner diameter of the tube, a second portion having an inner diameter greater than the inner diameter of the first portion, and a loading lumen extending from the first portion through the second portion.

Methods of implanting a prosthetic heart valve into a patient's heart using the heart valve delivery system are also disclosed.

BRIEF DESCRIPTION OF THE DRAWINGS

FIGS. 14A-14E illustrate a method of delivering the prosthetic valve into a heart using the delivery device of FIG. 11 and the inserter of FIG. 12A.

FIG. 15 is a side view of a funnel for loading the prosthetic valve into a second arrangement of the deploying device of FIG. 11.

DETAILED DESCRIPTION

As used herein, the term "proximal," when used in connection with a delivery device or components of a delivery device, refers to the end of the device closer to the user of the device when the device is being used as intended. On the other hand, the term "distal," when used in connection with a delivery device or components of a delivery device, refers to the end of the device farther away from the user when the device is being used as intended. As used herein, the terms "substantially," "generally," "approximately," and "about" are intended to mean that slight deviations from absolute are included within the scope of the term so modified.

Figure 1:
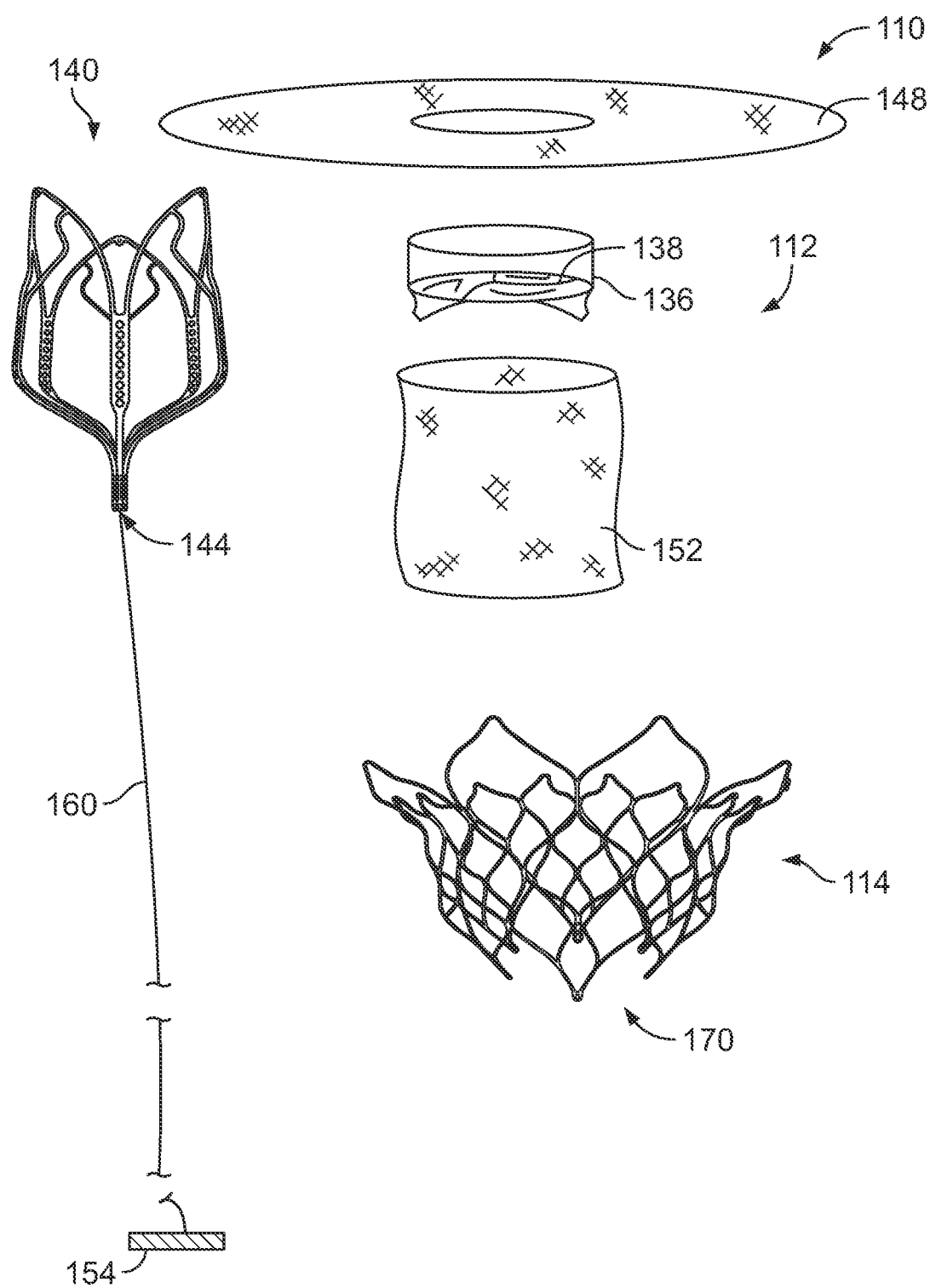
FIG. 1 is an exploded view of an exemplary prosthetic cardiovascular valve.

An exemplary prosthetic heart valve 110 as may be used with various embodiments of the present disclosure is shown in an exploded view in FIG. 1. Valve 110 includes an inner structure or assembly 112 and an outer structure or assembly 114. Valve 110 may be coupled to a tether 160 and a collapsible tether anchor 154.

Inner assembly 112 includes an inner frame 140, outer cylindrical wrap 152, and leaflet structure 136 (including articulating leaflets 138 that define a valve function). Leaflet structure 136 may be sewn to inner frame 140, and may use parts of inner frame 140 for this purpose. Inner assembly 112 is disposed and secured within outer assembly 114, as described in more detail below.

Outer assembly 114 includes outer frame 170. Outer frame 170 may also have in various embodiments an outer frame cover of tissue or fabric (not pictured), or may be left without an outer cover to provide exposed wireframe to facilitate in-growth of tissue. Outer frame 170 may also have an articulating collar or cuff (not pictured) covered by a cover 148 of tissue or fabric.

Tether 160 is connected to valve 110 by inner frame 140. Thus, inner frame 140 includes tether connecting or clamping portion 144 by which inner frame 140, and by extension valve 110, is coupled to tether 160.

Figure 2:
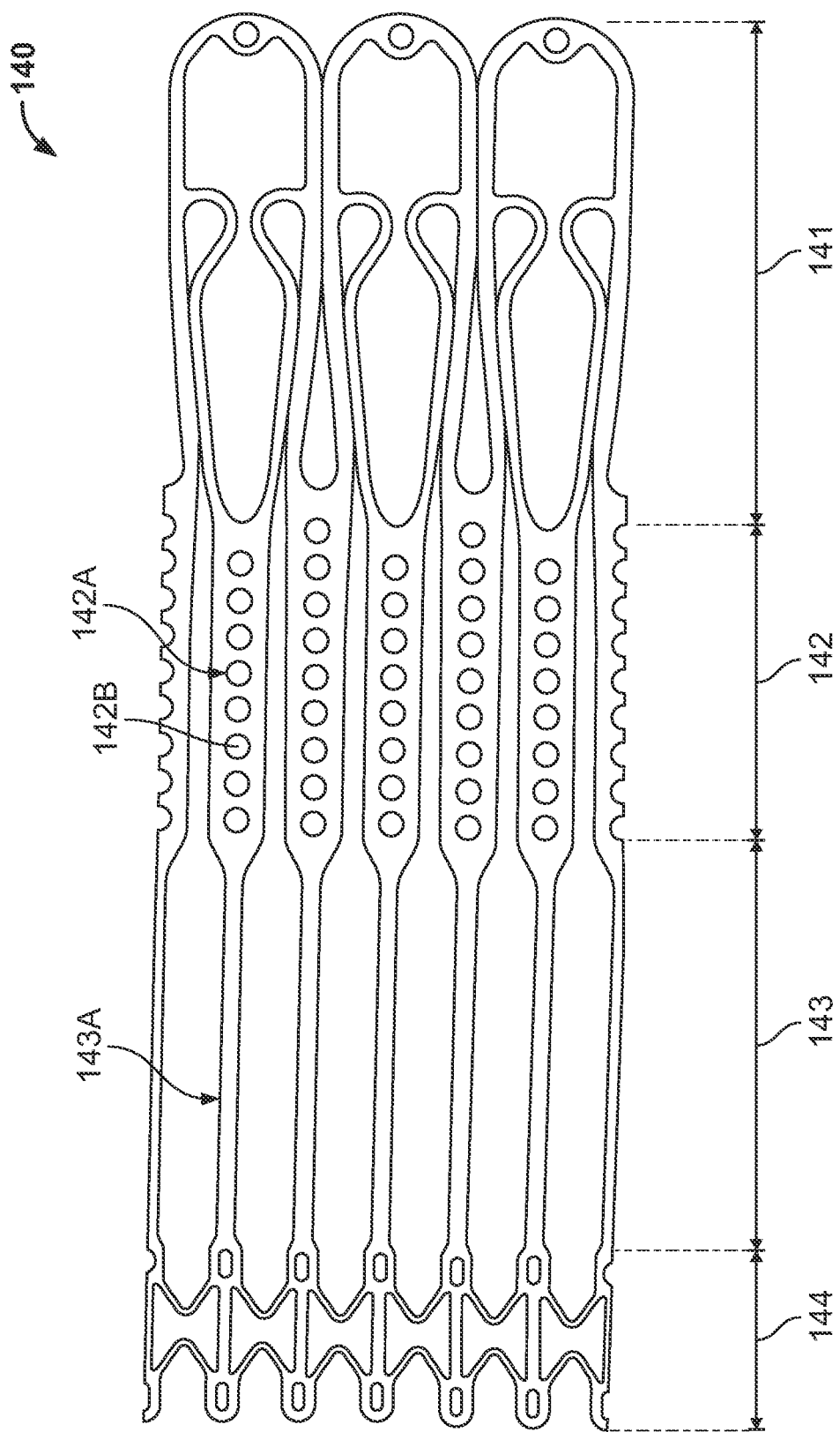
FIG. 2 is an opened and flattened view of an unexpanded inner frame of the prosthetic valve.
Figure 3:
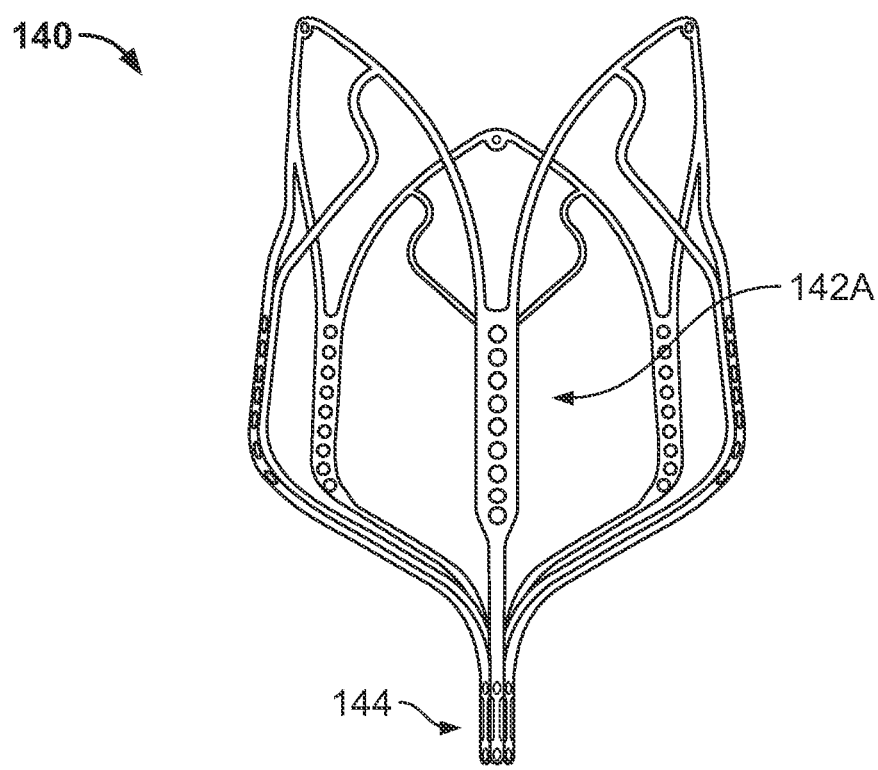
FIGS. 3 and 4 are side and bottom views, respectively, of the inner frame of FIG. 2 in an expanded configuration.
Figure 4:
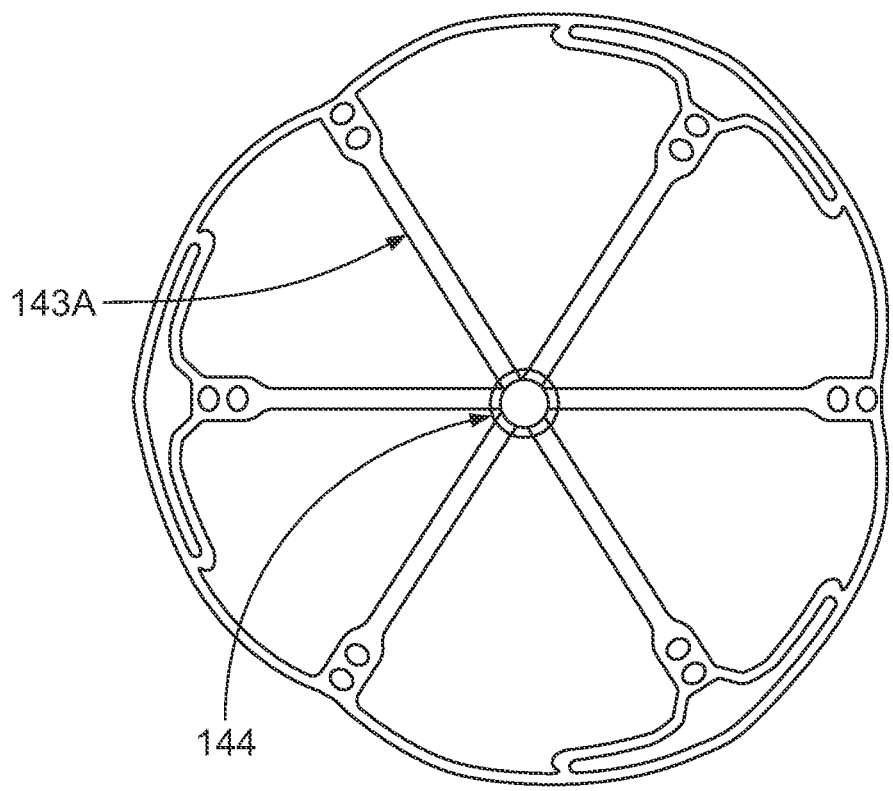

Inner frame 140 is shown in more detail in FIGS. 2-4. Inner frame 140 can be formed from a milled or laser-cut tube of a shape-memory material such as, for example, nitinol. Inner frame 140 is illustrated in FIG. 2 in an undeformed, initial state, i.e., as milled or laser-cut, but cut longitudinally and unrolled into a flat sheet for ease of illustration. Inner frame 140 is shown fully deformed, i.e., to the final, deployed configuration, in the side view and bottom view in FIGS. 3 and 4, respectively. Inner frame 140 can be divided into four portions corresponding to functionally different portions of inner frame 140 in final form: apex portion 141, body portion 142, strut portion 143, and tether clamp portion 144. Strut portion 143 includes six struts, such as strut 143A, which connect body portion 142 to tether clamp portion 144. A greater or lesser number of struts is contemplated herein.

Connecting portion 144 includes longitudinal extensions of the struts, connected circumferentially by pairs of micro-V's. Connecting portion 144 is configured to be radially collapsed by application of a compressive force, which causes the micro-V's to become more deeply V-shaped, with the vertices moving closer together longitudinally and the open ends of the V shapes moving closer together circumferentially. When collapsed, connecting portion 144 can clamp or grip one end of tether 160, either connecting directly onto a tether line (e.g., braided filament line) or onto an intermediate structure, such as a polymer or metal piece that is, in turn, firmly fixed to the tether line. The foregoing is merely exemplary and other techniques can be used to connect tether 160 to connecting portion 144.

In contrast to connecting portion 144, apex portion 141 and body portion 142 are configured to be expanded radially. Strut portion 143 forms a longitudinal connection, and radial transition, between the expanded body portion 142 and the compressed connecting portion 144.

Body portion 142 includes six longitudinal posts, such as post 142A, although the body portion may include a greater or lesser number of such posts. The posts can be used to attach leaflet structure 136 to inner frame 140, and/or can be used to attach inner assembly 112 to outer assembly 114, such as by connecting inner frame 140 to outer frame 170. In the illustrated example, posts 142A include apertures 142B through which connecting members (such as suture filaments and/or wires) can be passed to couple the posts to other structures.

Figure 5:
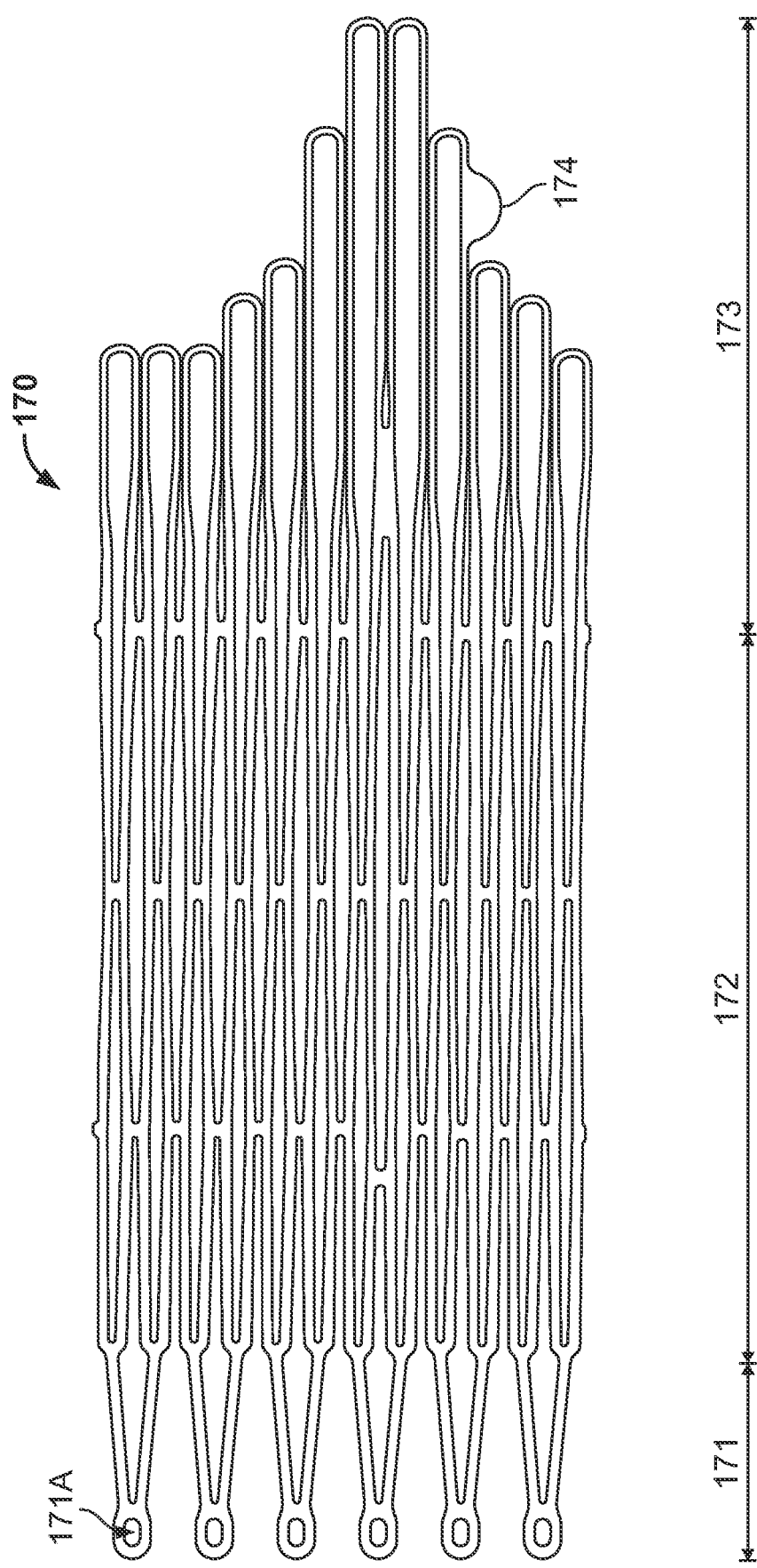
FIG. 5 is an opened and flattened view of an unexpanded outer frame of the prosthetic valve.
Figure 6:
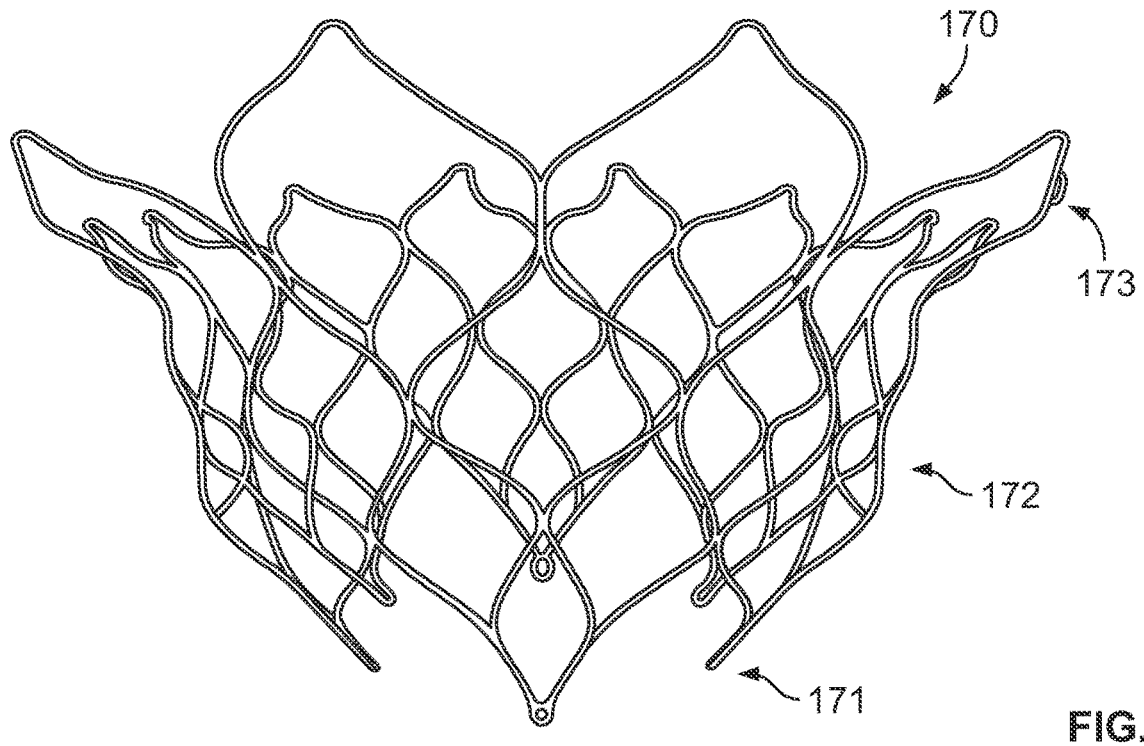
FIGS. 6 and 7 are side and top views, respectively, of the outer frame of FIG. 5 in an expanded configuration.
Figure 7:
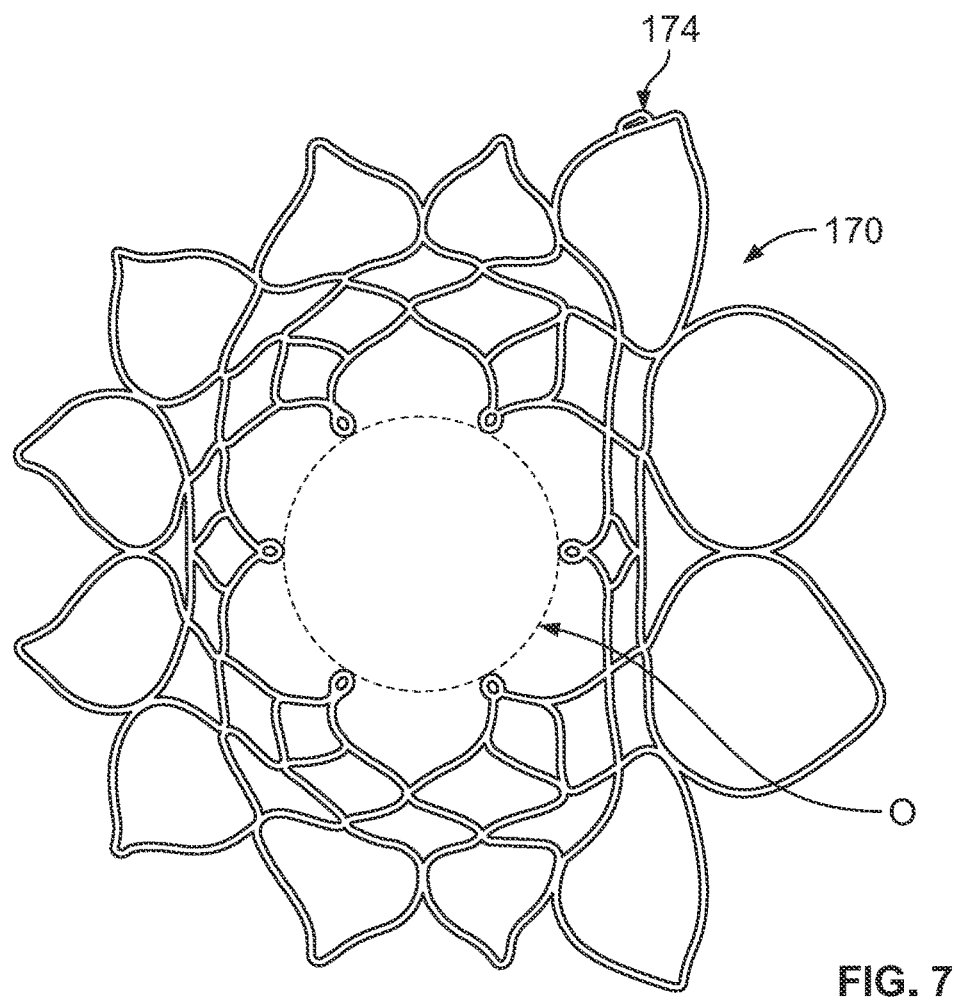

Outer frame 170 of valve 110 is shown in more detail in FIGS. 5-7. Outer frame 170 can be formed from a milled or laser-cut tube of a shape-memory material such as, for example, nitinol. Outer frame 170 is illustrated in FIG. 5 in an undeformed, initial state, i.e., as milled or laser-cut, but cut longitudinally and unrolled into a flat sheet for ease of illustration. Outer frame 170 can be divided into a coupling portion 171, a body portion 172, and a cuff portion 173, as shown in FIG. 5. Coupling portion 171 includes multiple openings or apertures 171A by which outer frame 170 can be coupled to inner frame 140, as discussed in more detail below.

Cuff portion 173 may include an indicator 174. In one example, indicator 174 is simply a broader portion of the wire frame element of cuff portion 173, i.e., indicator 174 is more apparent in radiographic or other imaging modalities than the surrounding wireframe elements of cuff portion 173. In other examples, indicator 174 can be any distinguishable feature (e.g., protrusion, notch, etc.) and/or indicia (e.g., lines, markings, tic marks, etc.) that enhance the visibility of the part of cuff portion 173 on which it is formed, or to which it is attached. Indicator 174 can facilitate the implantation of the prosthetic valve by providing a reference point or landmark that the operator can use to orient and/or position the valve (or any portion of the valve) with respect to the native valve annulus or other heart structure. For example, during implantation, an operator can identify (e.g., using echocardiography) indicator 174 when the valve 110 is situated in a patient's heart. The operator can therefore determine the location and/or orientation of the valve and make adjustments accordingly.

Outer frame 170 is shown fully deformed, i.e., to the final, deployed configuration, in the side view and top view in FIGS. 6 and 7, respectively. As best seen in FIG. 7, the lower end of coupling portion 171 forms a roughly circular opening (identified by "O" in FIG. 7). The diameter of this opening preferably corresponds approximately to the fully deformed diameter of body portion 142 of inner frame 140, to facilitate the coupling together of these two components of valve 110.

Figure 8:
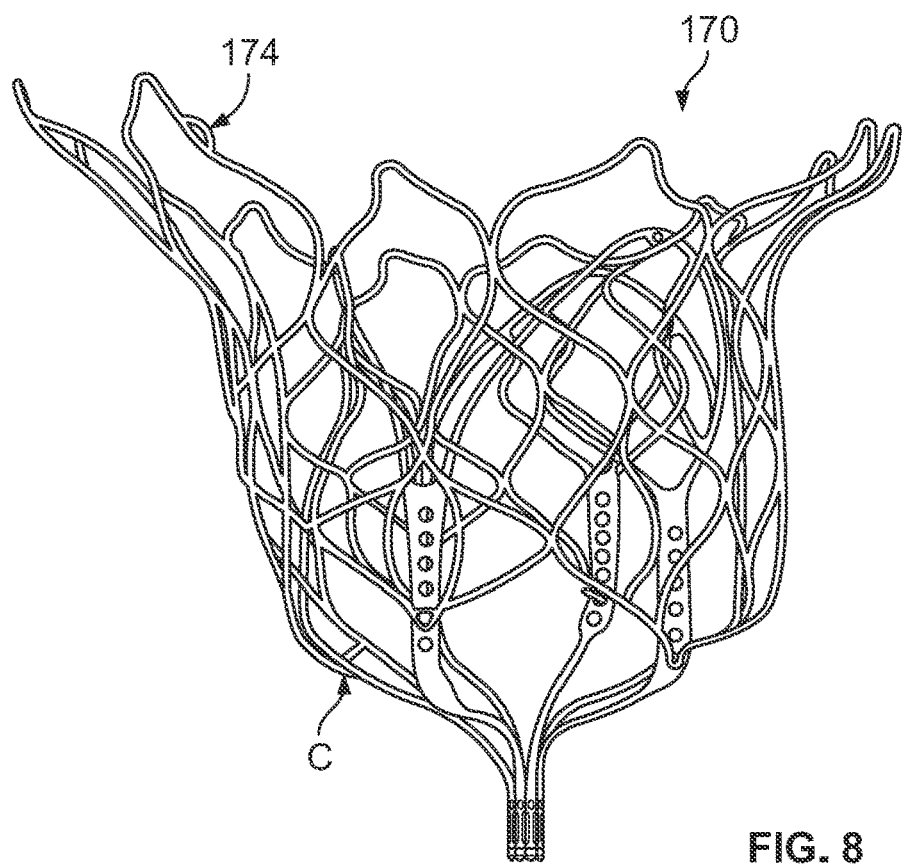
FIGS. 8-10 are side, front, and top views, respectively, of an assembly of the inner frame of FIGS. 2-4 and the outer frame of FIGS. 5-7.
Figure 9:
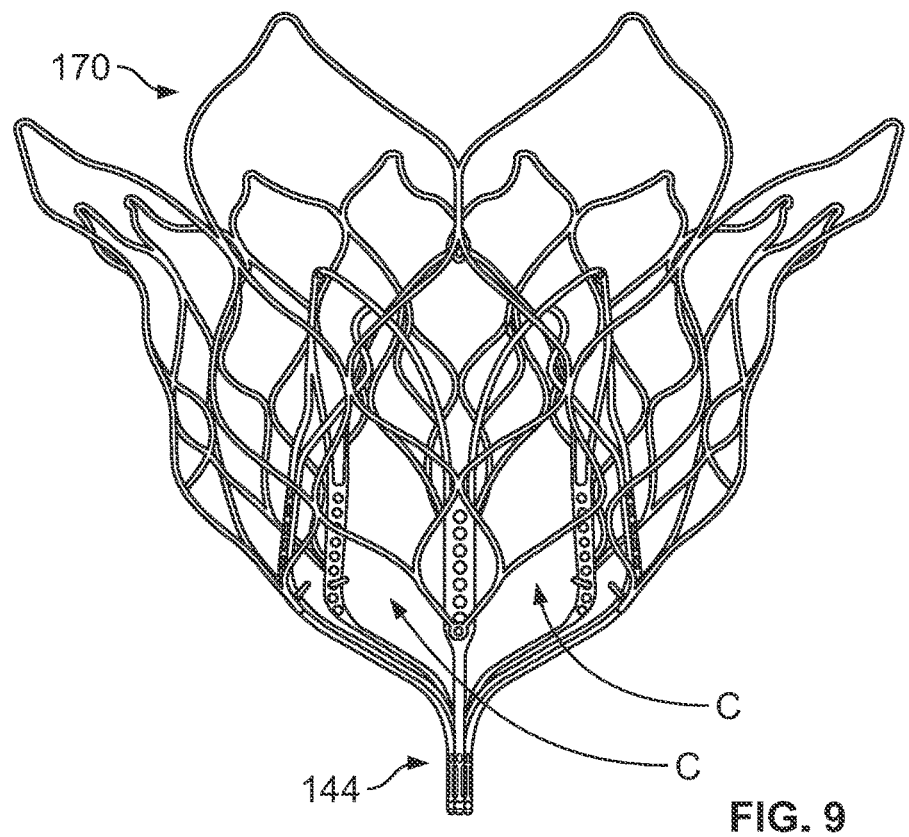
Figure 10:
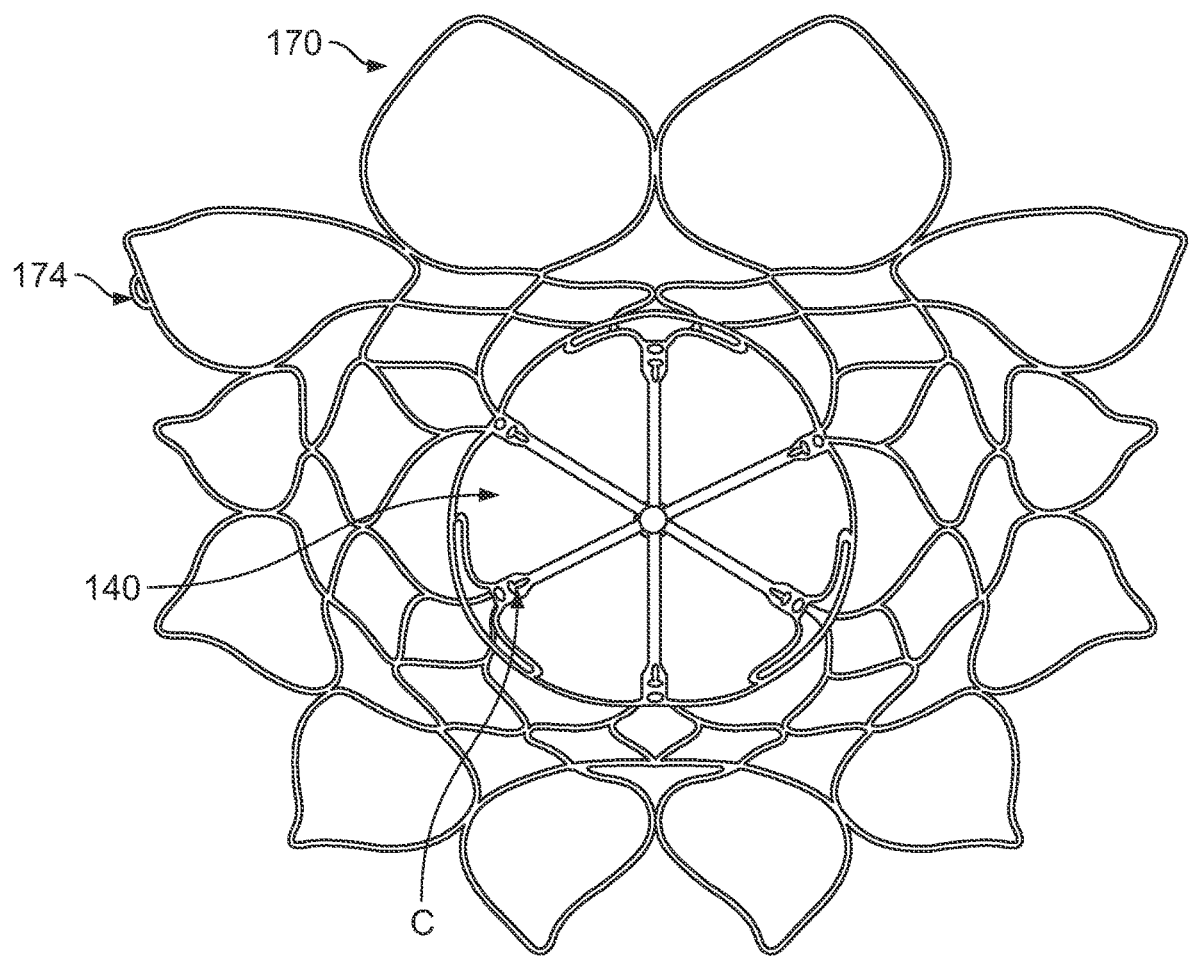

Outer frame 170 and inner frame 140 are shown coupled together in FIGS. 8-10 in front, side, and top views, respectively. The two frames collectively form a structural support for a prosthetic valve, such as valve 110 in FIG. 1. The frames support the valve leaflet structure 136 in the desired relationship to the native valve annulus, support the coverings for the two frames to provide a barrier to blood leakage between the atrium and ventricle, and couple to the tether 160 (by the inner frame 140) to aid in holding the prosthetic valve in place in the native valve annulus by the connection of the free end of the tether and tether anchor 154 to the ventricle wall, as described more fully below. The two frames are connected at six coupling points (representative points are identified as "C"). In this embodiment, the coupling of the frames is implemented with a mechanical fastener, such as a short length of wire, passed through an aperture 171A in coupling portion 171 of outer frame 170 and a corresponding aperture 142B in a longitudinal post 142A in body portion 142 of inner frame 140. Inner frame 140 is thus disposed within the outer frame 170 and securely coupled to it.

Figure 11:
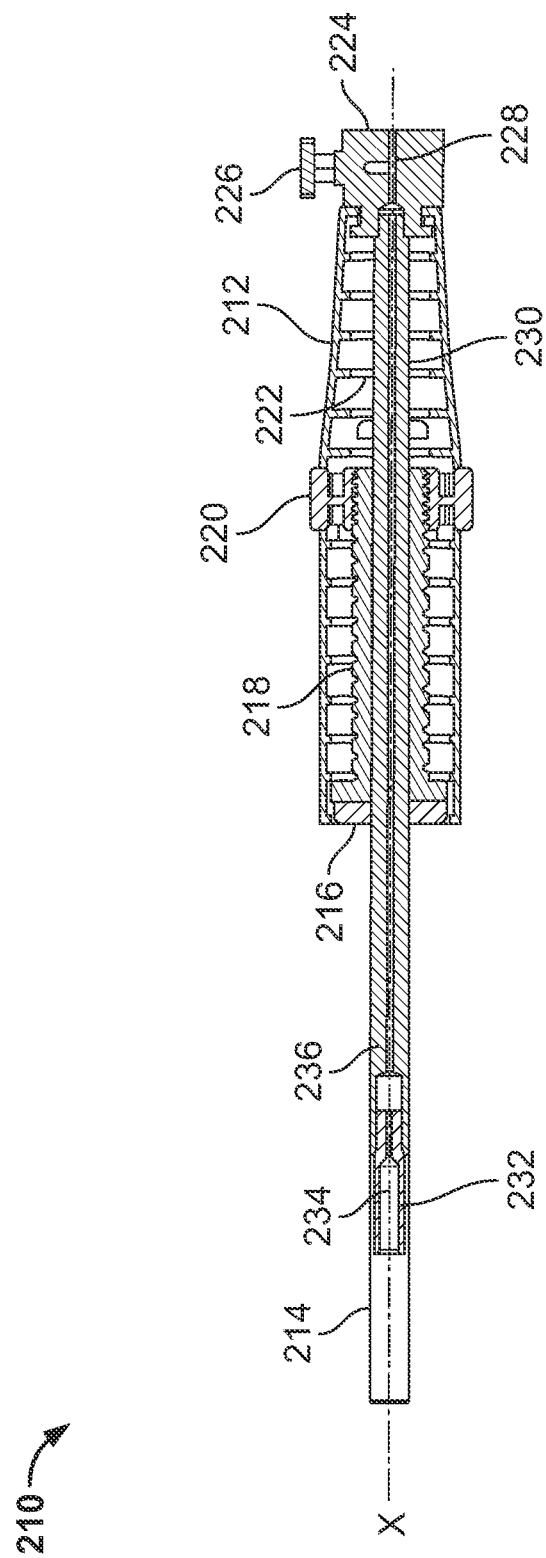
FIG. 11 is a longitudinal cross-sectional view of a device for deploying the prosthetic valve.

FIG. 11 shows an exemplary device 210 for delivering valve 110 to the native valve annulus and deploying the valve. Device 210 includes a handle 212 and a tube 214 extending distally along axis X from handle 212. A distal nose 216 is integrally formed with or fixedly connected to a proximal end of tube 214 and extends into handle 212. Tube 214 and distal nose 216 are movable together at least axially relative to handle 212, but tube 214 and distal nose 216 are mutually connected to be axially immovable relative to one another. Distal nose 216 includes an externally threaded shaft 218, which extends along axis X into handle 212 and is engaged with an axial adjustor 220. Adjustor 220 is an internally threaded ring rotatably connected to handle 212 and centered on axis X. Adjustor 220 may be rotated about axis X and about threaded shaft 218 while handle 212 is held immobile to extend or retract distal nose 216 relative to handle 212, thereby moving tube 214 between a fully extended position, shown in FIG. 11, and a fully retracted position in which threaded shaft 218 extends into cavity 222 provided within handle 212.

Device 210 includes a pin block 224 at a proximal end of handle 212, which may limit axial movement of distal nose 216 and tube 214. For example, the fully retracted position may be a position at which the proximal end of threaded shaft 218 abuts a distal surface of pin block 224. Pin block 224 has a threaded bore 228 extending in a direction generally perpendicular to axis X. A set screw 226 in bore 228 may be adjusted radially to selectively engage or disengage tether anchor 154 or tether 160 of valve 110, which may extend across bore 228.

A shaft 230 positioned in handle 212 has one end mounted to pin block 224 and extends distally along axis X where it is telescopically received within tube 214. A retainer 232 disposed at a distal end of shaft 230 has an interior space 234 for accommodating and supporting part of valve 110. For example, valve 110 may be loaded in device 210 such that part or all of any one of or any combination of inner frame 140, clamping portion 144, or tether 160 are disposed within the interior space 234 of retainer 232. Shaft 230 further includes a lumen 236 extending through its entire length that communicates at one end with bore 228 and at the other end with interior space 234, thereby enabling tether 160 to extend from a valve 110 loaded distally of retainer 232 to bore 228. In this example, shaft 230 is axially immovable relative to handle 212, such that the retainer 232 at the distal end of shaft 230 is at a fixed position relative to handle 212. However, any axial movement of tube 214 and distal nose 216 relative to handle 212 will result in a similar movement of tube 214 and distal nose 216 relative to shaft 230. Thus, as tube 214 is retracted proximally, the distal end of tube 214 will move closer to retainer 232, and as tube 214 is extended distally, the distal end of tube 214 will move farther from retainer 232.

In the fully extended position, tube 214 extends distally beyond a distal-most point of the retainer 232 such that shaft 230 and retainer 232 are entirely contained within handle 212 and tube 214. When tube 214 is in the fully retracted position, retainer 232 and part of shaft 230 extend distally out of tube 214. A valve 110 loaded within the distal end of tube 214 would be radially constrained while tube 214 is in an extended position overlying the valve, but would be free to expand upon movement of tube 214 to a retracted position in which the valve is exposed. Valve 110 may therefore be deployed after being collapsed and loaded into the distal end of tube 214 by moving tube 214 from the fully extended position to a retracted position while shaft 230 and valve 110 remain in a fixed position. Such a method of deployment provides a significant degree of control to a surgeon operating device 210, as device 210 can be manipulated to position and maintain valve 110 at an intended implanting location prior to and throughout deployment.

Materials envisioned for construction of device 210 are generally sufficiently rigid or semi-rigid to allow manipulation of device 210 without flexure, while also being biocompatible. Examples of such materials include stainless steel and polyetheretherketone (PEEK), which may be used to form any combination of the components of device 210 described above. For example, as described more fully below tube 214 and shaft 230 may be constructed from stainless steel, while retainer 232 may be constructed from PEEK. The use of other biocompatible metals and polymers and combinations thereof is also contemplated.

Figure 12A:
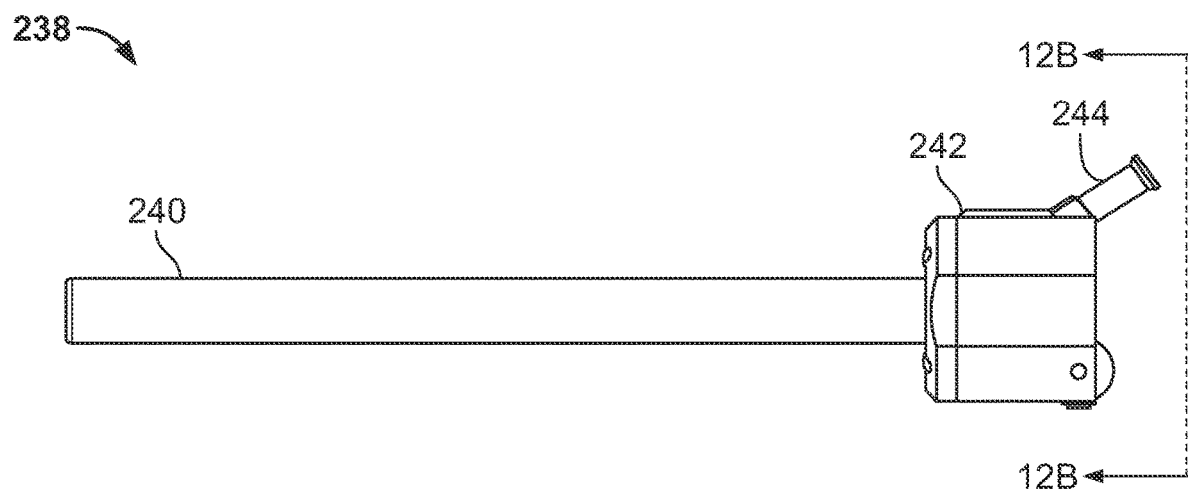
FIG. 12A is a side view of an inserter for the deploying device of FIG. 11.
Figure 12B:
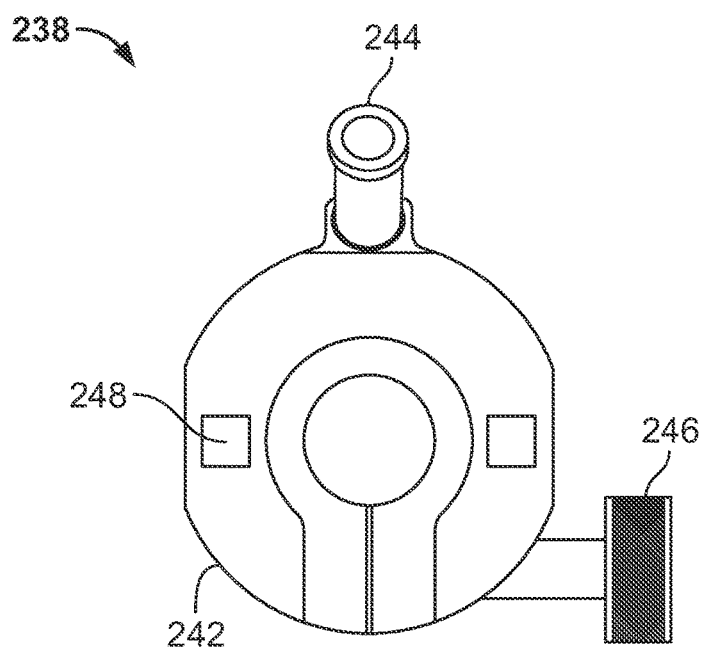
FIG. 12B is an end view of the inserter of FIG. 12A.

FIGS. 12A and 12B illustrate an inserter 238 including a sheath 240 and a collar 242. Sheath 240 is cannular and has an inner diameter slightly larger than the outer diameter of tube 214. Collar 242 is attached to or integrally formed with the proximal end of sheath 240 and includes features, such as a passive seal or valve (not pictured), for maintaining hemostatic pressure and preventing air emboli when inserter 238 is inserted into a patient's heart. Port 244, for example, extends from collar 242 in a direction transverse to sheath 240 and may include a pressure regulating valve or may be connected to external pressure regulating apparatus. In addition or in the alternative, port 244 may provide a passageway for the introduction and removal of ancillary instruments. For example, a dilator (not shown), such as a saline balloon, may be inserted through port 244 and out from the distal end of sheath 240 to provide an atraumatic tip while inserter 238 is advanced within a patient.

Figure 13A:
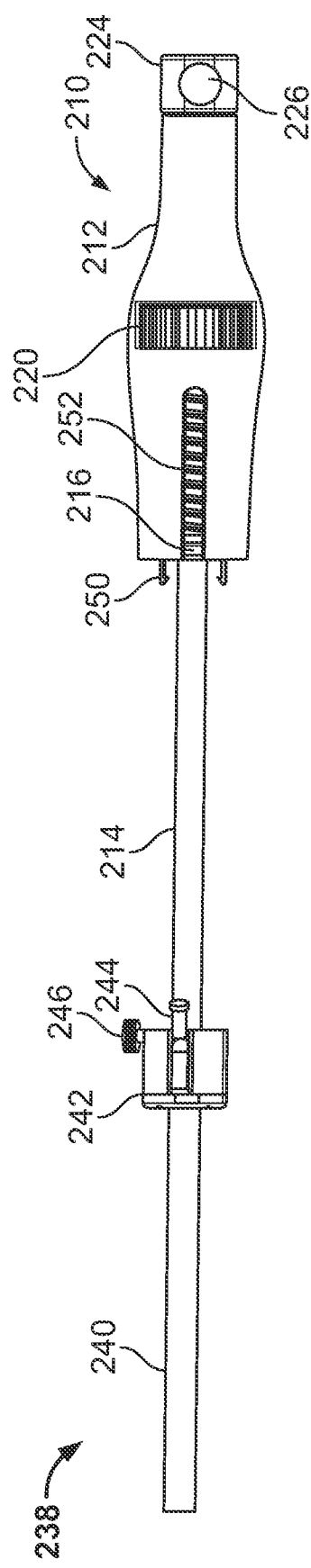
FIGS. 13A and 13B illustrate aligning and coupling the deploying device of FIG. 11 to the inserter of FIG. 12A.
Figure 13B:
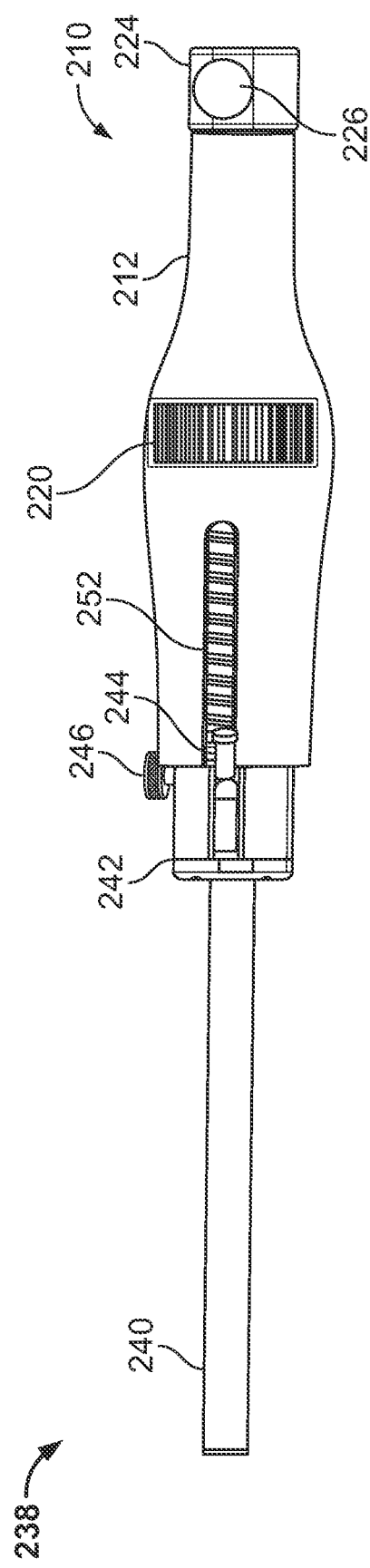

Turning to FIGS. 13A and 13B with continued reference to FIGS. 12A and 12B, the distal end of tube 214 may be inserted through collar 242 and into the proximal end of sheath 240, and inserter 238 may then be coupled to device 210 to maintain full coverage of tube 214 by sheath 240. Collar 242 and distal nose 216 include features for releasably coupling inserter 238 to delivery device 210. More particularly, collar 242 includes a clamp screw 246 and first coupling features 248, while distal nose 216 includes distally extending second coupling features 250 for engaging first coupling features 248. In one embodiment, second coupling features 250 may be semi-rigid, elastically deformable tapered hook arms, and first coupling features 248 may be complimentary recesses within collar 242, with each recess including a shoulder for engaging a hook arm. As tube 214 is advanced to a fully covered position within sheath 240, second coupling features 250 are advanced into first coupling features 248 such that second coupling features 250 deform slightly before snapping into hooked engagement with first coupling features 248. Tightening clamp screw 246 against tube 214 secures sheath 240 to tube 214. In alternative embodiments, first and second coupling features 248, 250 may be reversed, with first coupling features 248 on distal nose 216 and second coupling features on collar 242. Still further, any type of releasable coupling features other than those described above may be used to mutually engage and restrain relative axial movement between tube 214 and sheath 240 after tube 214 has been fully advanced into sheath 240.

As collar 242 is directly coupled to distal nose 216, the retraction or extension of tube 214 and distal nose 216 will result in a corresponding retraction or extension of inserter 238. To accommodate the retraction of inserter 238, collar 242 has a diameter that is similar to or smaller than the diameter of distal nose 216 so that collar 242 will be receivable within the distal end of handle 212. Additionally, handle 212 includes a slot 252 extending proximally from the distal end of handle 212 to accommodate port 244 as tube 214 and inserter 238 are retracted. Handle 212 includes a second slot (not visible in the views provided by the Figures), to accommodate clamp screw 246 as tube 214 and inserter 238 are retracted. The fully retracted position may be the point at which port 244 abuts the proximal end of slot 252.

Figure 14E:
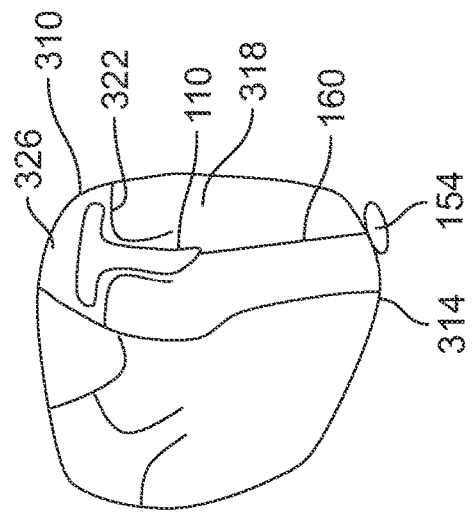
Figure 14D:
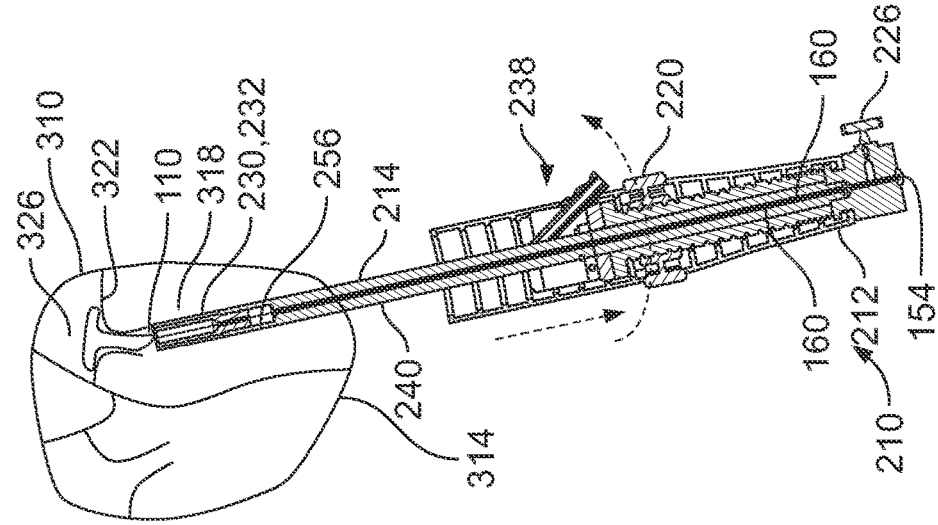

FIGS. 14A-14E schematically illustrate the delivery of prosthetic heart valve 110 into heart 310 using delivery device 210 and inserter 238. As shown in FIG. 14A, a distal end of sheath 240 is inserted into heart 310 near the apex 314 of the heart 310. Sheath 240 is advanced through ventricle 318 of the heart 310 toward native valve 322 to be replaced. In one embodiment of the delivery process, ventricle 318 may be the left ventricle and valve 322 may be the mitral valve. Dilator 254, such as a saline balloon, may extend from the distal end of sheath 240 to serve as an atraumatic tip to prevent injury to cardiac tissue, such as chordae tendineae or myocardium, as sheath 240 advances. Turning to FIG. 14B, inserter 238 may be advanced until the distal end of sheath 240 extends at least partially through native valve 322 into atrium 326. At this point, dilator 254 may be removed, for example, through port 244 and the distal end of tube 214 of device 210 may be inserted through collar 242 and into the proximal end of sheath 240. Prosthetic valve 110 is loaded in the distal end of tube 214, with tether 160 extending proximally through the lumen 236 of shaft 230 from valve 110 to tether anchor 154, which is retained at the proximal end of handle 212 by set screw 226.

Figure 14C:
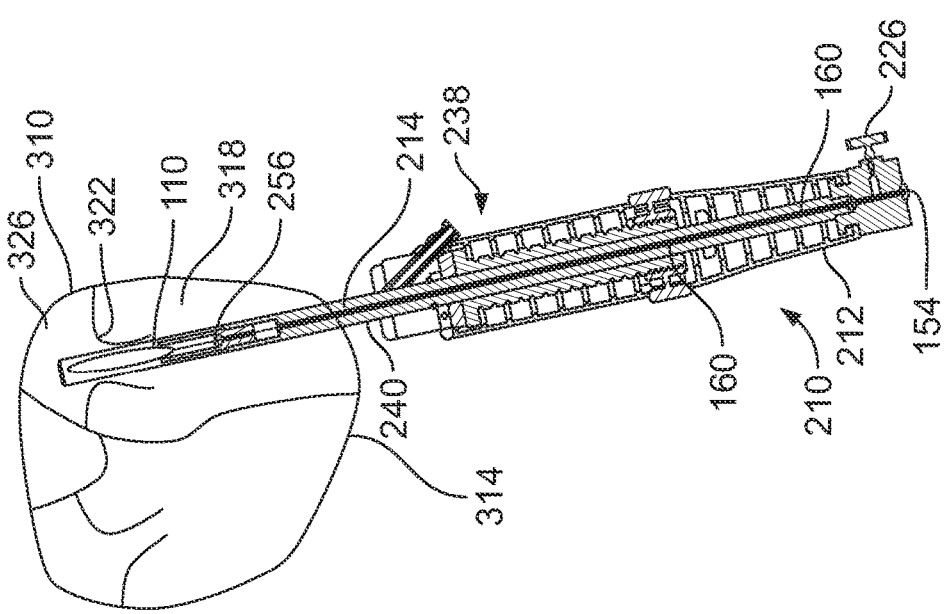

Tube 214 may be advanced distally through sheath 240 while inserter 238 is held stationary until the distal nose 216 of handle 212 reaches collar 242 and second coupling features 250 engage in first coupling features 248 to couple device 210 to inserter 238. At this juncture, the distal end of tube 214 will be positioned such that prosthetic valve 110 is disposed at least partially within the annulus of native valve 322, as shown in FIG. 14C. Tube 214 is next retracted along with inserter 238 by rotating adjustor 220 relative to handle 212 in the example illustrated in FIG. 14D. The retraction of tube 214 and inserter 238 relative to stationary shaft 230 moves the open distal ends of tube 214 and shaft 240 toward prosthetic valve 110. When tube 214 and inserter 238 are in the fully retracted position, retainer 232 and part of shaft 230 will protrude distally from tube 214 and sheath 240, and prosthetic valve 110 will no longer be constrained. Prosthetic valve 110 will then expand or unfold into an implanted position within the annulus of native valve 322.

Finally, tether anchor 154 is released by loosening set screw 226 and retracting device 210 and inserter 238, whereupon tether 160 and tether anchor 154 are pulled distally through the lumen 236 of shaft 230 toward and out from retainer 232. Upon its release from lumen 236, tether anchor 154 will expand and seat against an outer surface of heart 310 at apex 314, as shown in FIG. 14E. Prosthetic valve 110 will then settle into a final position and will be prevented from displacement by tether anchor 154.

FIG. 15 shows a loading funnel 256 according to another aspect of the disclosure. Funnel 256 has a distal end 258, a proximal end 260, and a plurality of apertures 262, which may be fastener apertures, near proximal end 260. Apertures 262 may be used to hold funnel 256 in place relative to device 210 throughout loading.

Figure 16B:
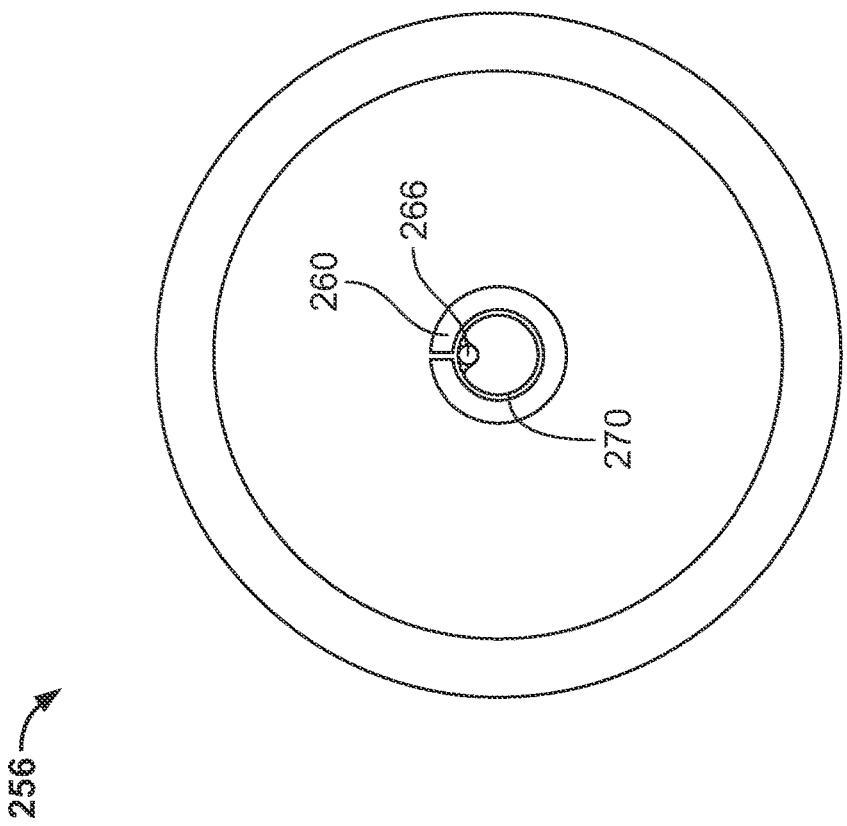
FIGS. 16A and 16B are opposite end views of the funnel of FIG. 15.
Figure 16A:
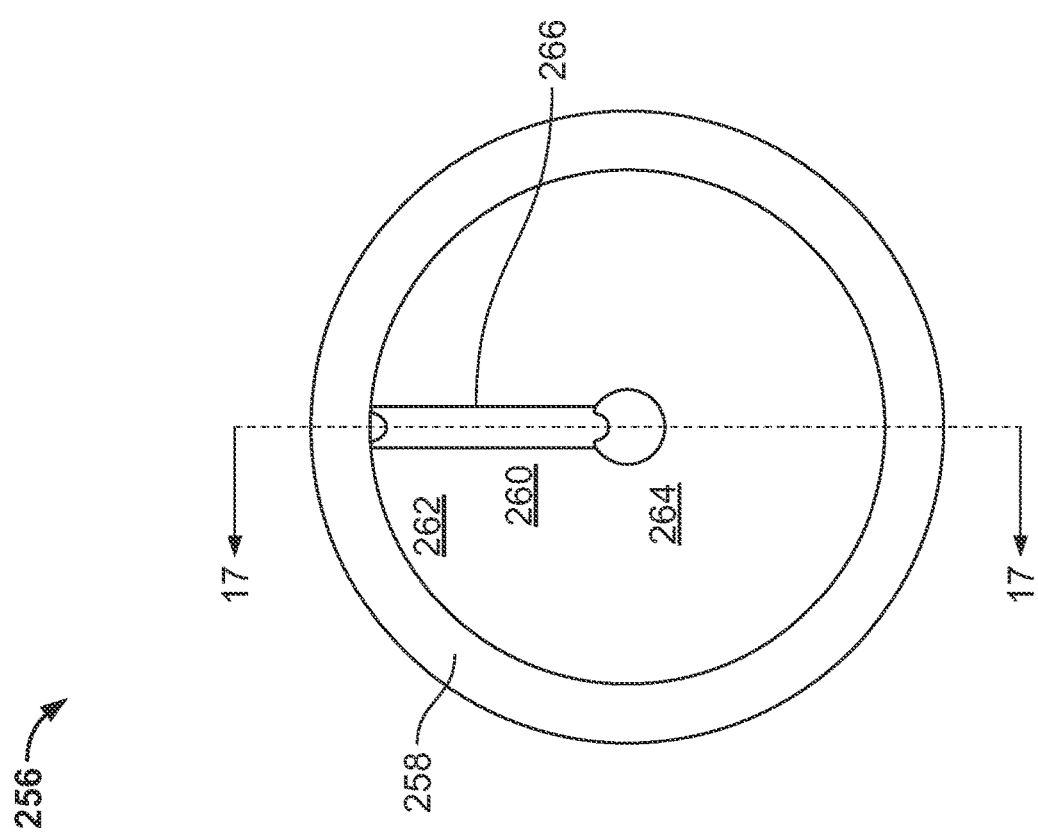

FIGS. 16A and 16B illustrate funnel 256 from distal end 258 and proximal end 260, respectively. Funnel 256 defines a tapered loading space 264 that opens at distal end 258 and tapers toward proximal end 260. A loading lumen 266 extends along the interior of funnel 256 between distal end 258 and proximal end 260.

Figure 17:
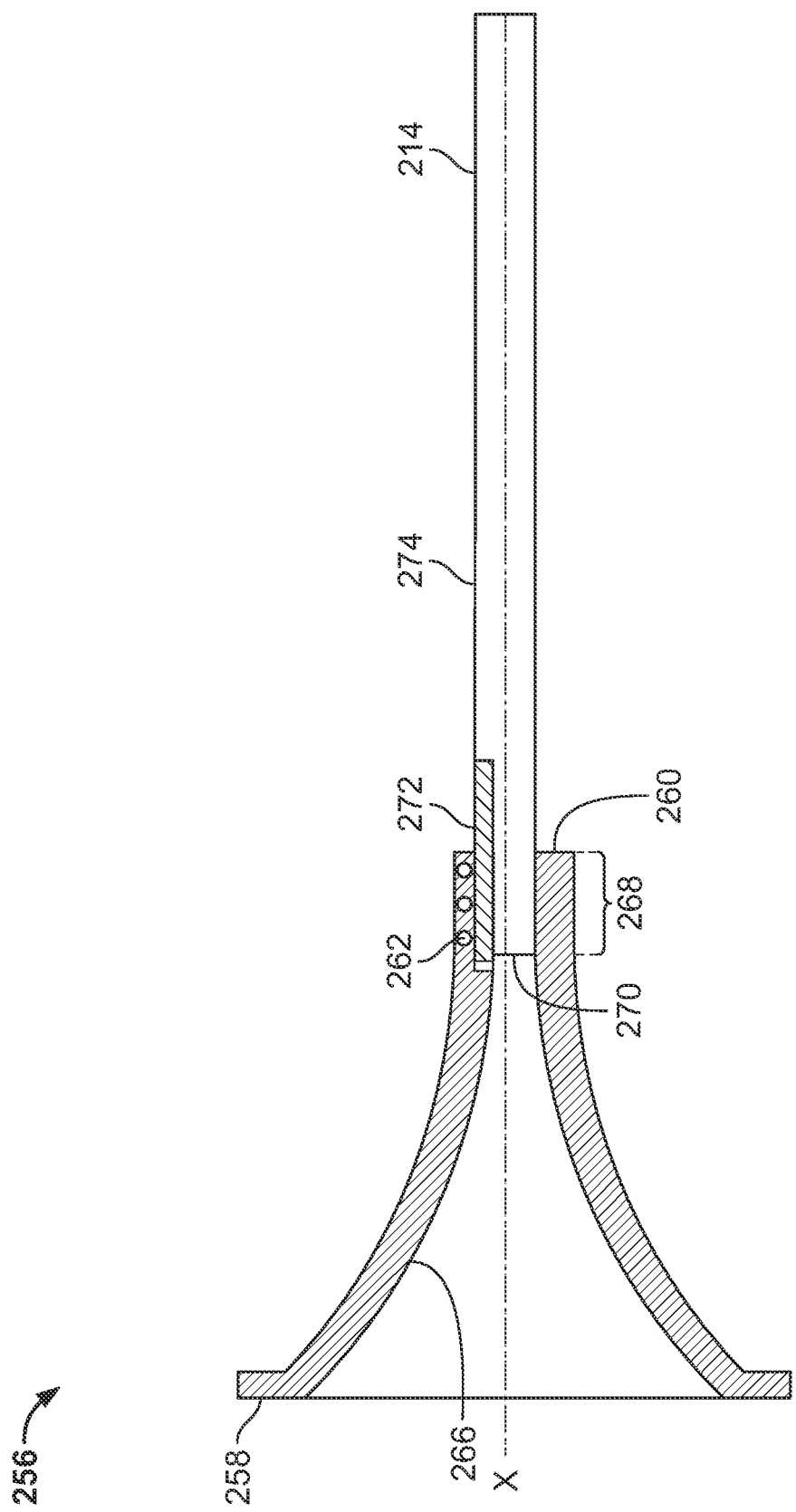
FIG. 17 is a longitudinal cross-sectional view of the funnel of FIG. 15 assembled to the deploying device of FIG. 11 according to the second arrangement.

Turning to FIG. 17, funnel 256 may be aligned along axis X and assembled to the distal end of tube 214. Loading space 264 tapers to an inner diameter at a step 270 that is equal or approximately equal to the inner diameter of tube 214. A fitting portion 268 extending from proximal end 260 to step 270 has a slightly larger inner diameter that is equal or approximately equal to the outer diameter of tube 214. Inserting tube 214 into fitting portion 268 therefore creates a smooth transition from loading space 264 to the interior of tube 214. The smooth transition allows prosthetic valve 110 to be safely loaded into tube 214. For example, with tube 214 in the fully retracted position and funnel 256 located at the distal end of tube 214, prosthetic valve 110 may be folded or compressed within loading space 264 with tether 160 extending through proximal end 260 and shaft 230 such that tether anchor 154 is fixed at the proximal end of device 210 as described above. Advancing tube 214 to the fully extended position pushes funnel 256 away from handle 212 and further compresses prosthetic valve 110 as it is drawn proximally through funnel 256 and into the distal end of tube 214.

Loading lumen 266 follows the tapered contour of loading space 264 but otherwise extends straight from fitting portion 268 to distal end 258. Its straight configuration enables loading lumen 266 to function as a guide to prevent rotation of prosthetic valve 110 while prosthetic valve 110 is being loaded into tube 214. For example, prosthetic valve 110 may be constructed or folded with a dent or groove complementary in shape to loading lumen 266 such that the dent or groove remains aligned with loading lumen 266 as funnel 256 moves relative to prosthetic valve 110.

Additionally, loading lumen 266 provides a guide for loading a balloon, such as dilator 254 described above, into device 210. For example, tube 214 may have a separate tube lumen 274 that is alignable with loading lumen 266 when tube 214 is assembled to funnel 256. Tube lumen 274 may or may not extend to the distal end of tube 214. In arrangements in which tube lumen 274 does not extend to the distal end of tube 214, as illustrated in FIG. 17, any balloon or dilator 254 deployed from tube lumen 274 would expand to occupy an entire diameter of tube 214 in the space between the distal end of tube lumen 274 and the distal end of tube 214. As a result of dilator 254 occupying the entire diameter of tube 214, any portion of dilator 254 protruding from distal end of tube 214 would tend to be centered on axis X.

Dilator 254 may be loaded through loading lumen 266 and into separate tube lumen 274 simultaneously with and in a similar manner to prosthetic valve 110. Loading a balloon dilator 254 into device 210 may obviate the need for inserter 238 in that tube 214 may be advanced within the patient with an atraumatic tip provided by the balloon, and, when no longer needed, the balloon may be withdrawn through tube lumen 274 while tube 214 is held stationary. Prosthetic valve 110 may then be deployed by retracting tube 214 proximally as described above. Certain arrangements of device 210 configured for use with funnel 256 are therefore used without inserter 238. For example, certain arrangements of device 210 configured for use with funnel 256 do not include features for accommodating inserter 238, such as cavity 222, slot 252, or second coupling features 250, and may have an adjustor 220 of a linear rather than rotating design. Similarly, certain arrangements of device 210 configured for use with inserter 238 are incompatible with funnel 256 and do not include tube lumen 274.

Figure 18B:
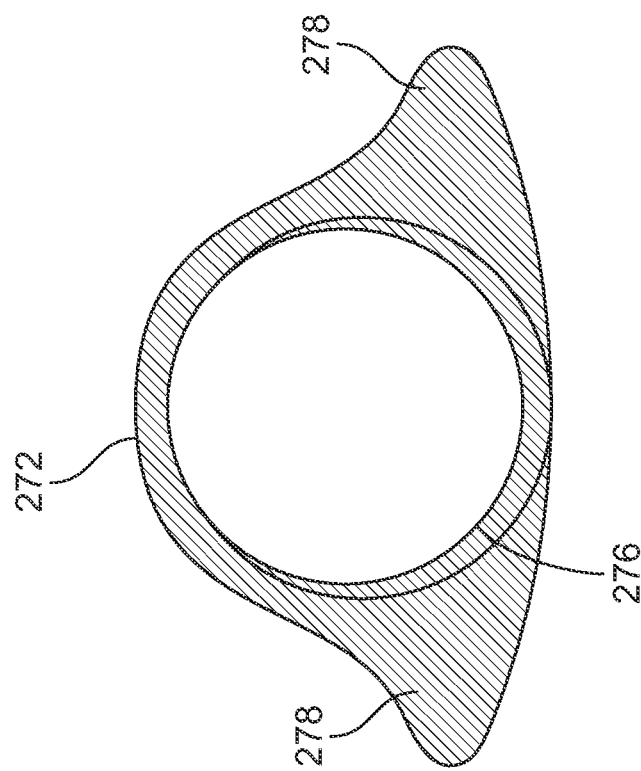
FIG. 18B is a transverse cross-sectional view of the bridge.
Figure 18A:
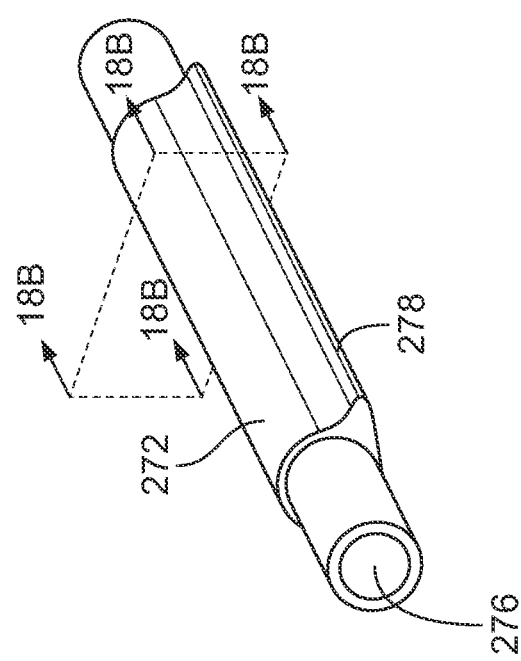
FIG. 18A is a perspective view of a bridge for connecting the funnel to the deploying device.

Turning to FIG. 18A, a bridge 272 may be used to align funnel 256 with, and secure funnel 256 to, tube 214. Bridge 272 has a bridge lumen 276 extending therethrough with an inner diameter equal to the inner diameters of loading lumen 266 and tube lumen 274. As shown in FIG. 17, loading lumen 266 does not extend flush to proximal end 260 of funnel 256, so bridge 272 and bridge lumen 276 act to connect loading lumen 266 to tube lumen 274 for loading a dilator 254 into tube 214. Bridge 272 may further include laterally extending wings 278 (FIG. 18B), which may fit corresponding slots or grooves (not illustrated) in tube 214 and funnel 256.

Figure 19B:
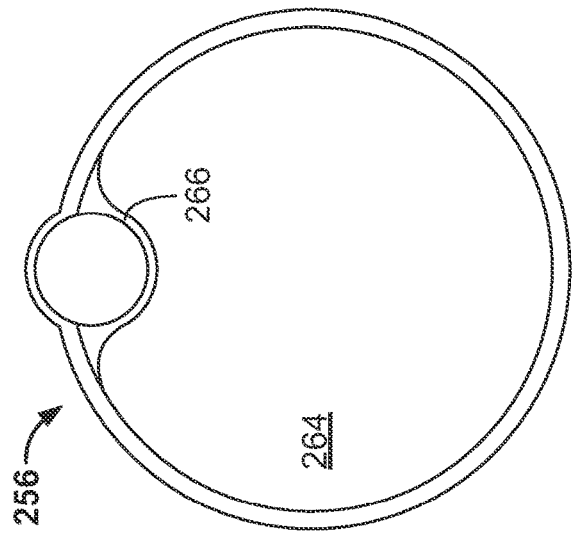
FIGS. 19A-19C are transverse cross-sectional views of various embodiments of the funnel.
Figure 19C:
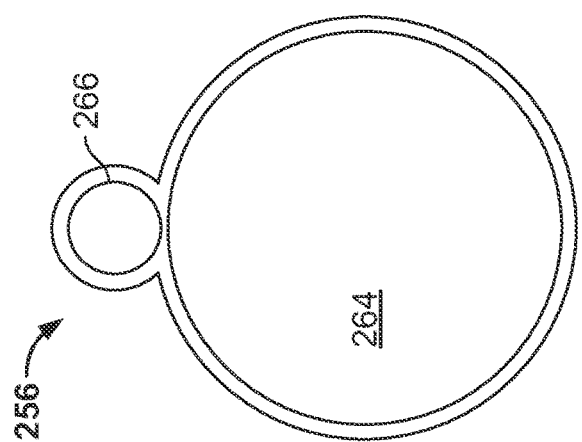
Figure 19A:
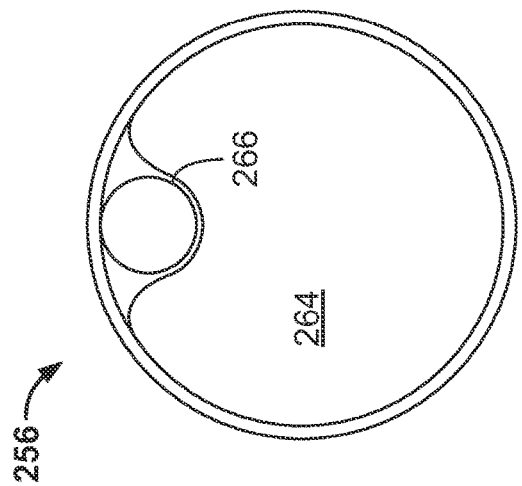

FIGS. 19A-19C illustrate transverse cross-sections of funnel 256 taken approximately through a midpoint of funnel 256 according to various embodiments. Loading lumen 266 may be disposed entirely within loading space 264 as illustrated in FIGS. 16A, 17 and 19A. Alternatively, loading lumen 266 may be disposed only partially within loading area 264 and partially within the wall of funnel 256 as shown in FIG. 19B, or entirely outside of loading space 264 as illustrated in FIG. 19C. In any of the foregoing examples, tube lumen 274 may be disposed within or outside of tube 214 to match the relationship of loading lumen 266 to loading space 264.

Figure 20:
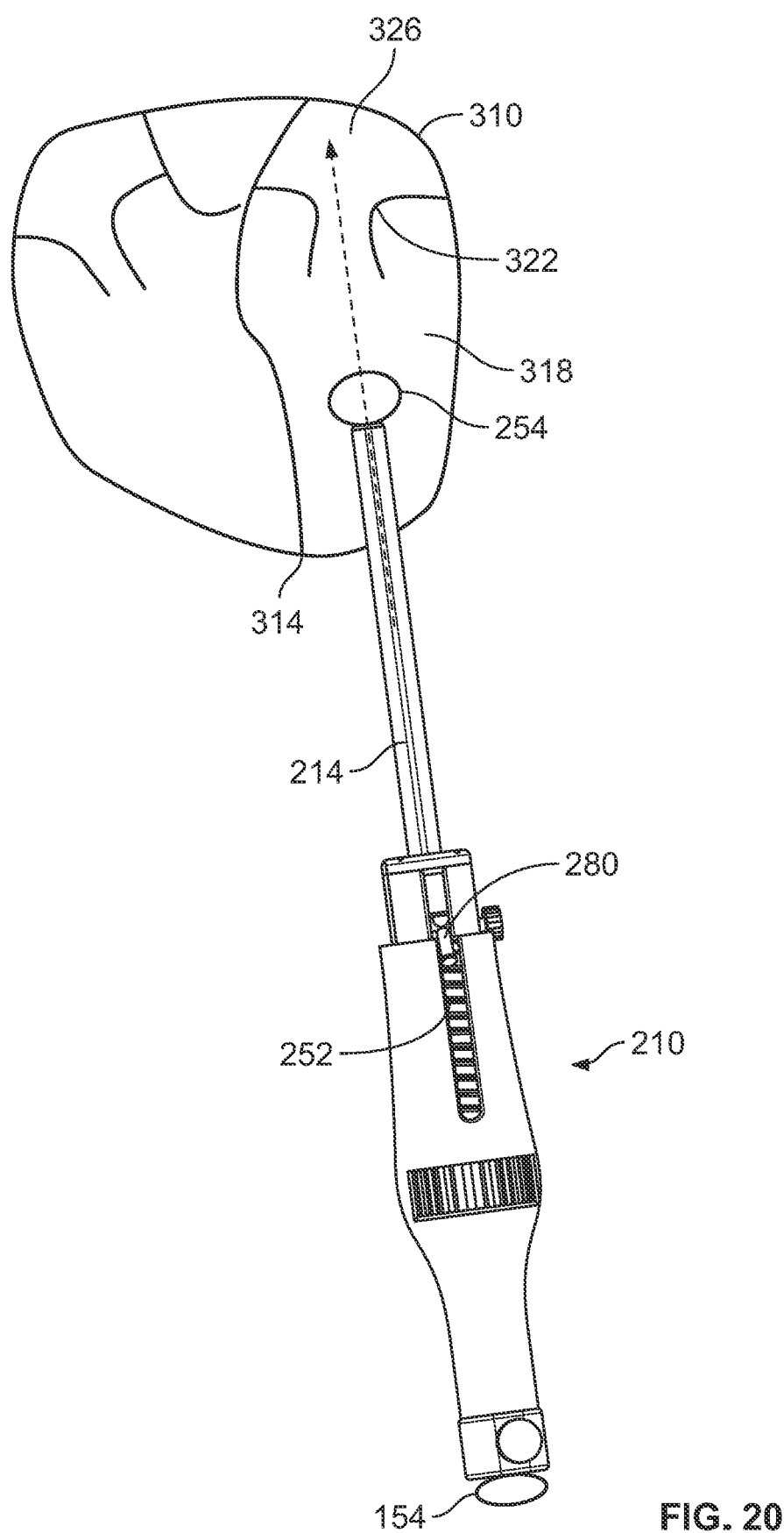
FIG. 20 illustrates a method of delivering the prosthetic valve into a heart using the deploying device according to the second arrangement.

Certain arrangements of device 210 configured for use with funnel 256 may therefore be used to deliver prosthetic valve 110 in a manner similar to the process illustrated in FIGS. 14A-14E. In such a process, dilator 254 may be inflated to extend from the distal end of tube lumen 274 to enable atraumatic insertion of the distal tip of tube 214 into ventricle 318, then through native valve 322 into atrium 326, as shown in FIG. 20. In such arrangement of device 210, a tube lumen port 280 in fluid communication with tube lumen 274 extends laterally from device 210. Tube lumen port 280 can be used to add or remove fluid within dilator 254. Tube lumen port 280 is accommodated by slot 252 in the same manner as port 244. Thus, after insertion of the distal tip of tube 214 to the proper depth within atrium 326 and withdrawal of dilator 254 into tube lumen 274 by evacuation of fluid from tube lumen port 280, delivery of prosthetic valve 110 can be achieved by steps like those described above with regard to FIGS. 14D and 14E. Particularly, adjustor 220 is rotated to withdraw tube 214, thus leaving prosthetic valve 110 free to expand and seat in its intended permanent position, similar to the step illustrated in FIG. 14D. Tether anchor 154 is then released by loosening set screw 226, and device 210 is removed to result in the same arrangement of valve 110 within heart 310 as shown in FIG. 14E.

To summarize the foregoing, disclosed is a heart valve delivery system including a handle; a shaft having a proximal end fixedly connected to the handle and extending distally along an axis away from the handle to a free end; and a tube surrounding the shaft, the tube having a proximal end connected to the handle and extending distally along the axis away from the handle to a distal end, the tube being axially movable relative to the shaft and the handle between a fully extended position at which the tube extends distally farther than the shaft, and a fully retracted position at which the shaft extends distally farther than the tube; and/or the heart valve delivery system may further include a distal nose fixedly connected to the proximal end of the tube, the distal nose including a threaded shaft extending proximally into the handle; and an internally threaded adjustor ring rotatably connected to the handle and threadedly connected to the threaded shaft such that rotation of the adjustor ring relative to the handle axially moves the tube between the fully extended position and the fully retracted position; and/or the heart valve delivery system may further include a retainer located at the free end of the shaft and having an interior space extending proximally from a distal end of the retainer; and/or a lumen may extend continuously from the proximal end of the shaft to the free end of the shaft; and/or the heart valve delivery system may further include a pin block at a proximal end of the handle; a bore extending through the pin block; and a locking element selectively movable to impinge upon or clear the bore; and/or the heart valve delivery system may further include an inserter having a tubular sheath with an inner diameter greater than an outer diameter of the tube; and a distal nose fixedly connected to the proximal end of the tube, the distal nose being couplable to the inserter to restrain axial movement of the inserter relative to the tube; and/or the inserter may include a port near a proximal end of the inserter, the port being in communication with an interior of the sheath and extending transverse to the sheath; and/or the heart valve delivery system may further include a storage lumen extending axially along the tube; and a funnel, the funnel including a first portion having an inner diameter equal to an inner diameter of the tube; a second portion having an inner diameter greater than the inner diameter of the first portion; and a loading lumen extending from the first portion through the second portion; and/or the heart valve delivery system may further include a bridge having a lumen extending therethrough, the lumen having a diameter at a first end equal to an inner diameter of the storage lumen and a diameter at another end equal to an inner diameter of the loading lumen; and/or the tube may include tube slots, the funnel may include funnel slots, and the bridge may include laterally extending wings that fit within the tube slots and the funnel slots such that the bridge may be received simultaneously in both the tube slots and the funnel slots to align the loading lumen with the channel and the storage lumen and to restrain rotation of the funnel about the axis relative to the tube; a method of implanting a prosthetic heart valve into a patient's heart using the heart valve delivery system may include inserting a distal end of the sheath into the heart; and inserting a distal end of the tube into the sheath; and/or the method may further include coupling the distal nose to the sheath; and retracting the tube to the fully retracted position; and/or the method may further include inflating a balloon disposed within the sheath such that part of the inflated balloon extends outward from the distal end of the sheath while advancing the sheath through the heart; and deflating the balloon and removing the balloon from the sheath prior to inserting the distal end of the tube into the sheath; and/or the method may further include loading a prosthetic heart valve into the tube before inserting the tube into the sheath; and/or the step of loading the prosthetic heart valve may include securing an anchor of the prosthetic heart valve to the handle; and/or the method may further include removing the sheath and the tube from the heart; and tightening the anchor against an outside of the heart after removing the sheath and the tube from the heart; and/or a method of loading a prosthetic heart valve into the heart valve delivery system may include axially aligning the first portion of the funnel with the distal end of the tube; rotationally aligning the loading lumen of the funnel with the storage lumen along the tube; disposing a prosthetic heart valve within the funnel and at a distal end of the shaft while the tube is in the fully retracted position; securing an anchor of the prosthetic heart valve to the handle to restrain relative movement between the prosthetic heart valve and the handle, the prosthetic heart valve being connected to the anchor by a tether extending through the tube; and extending the tube from the fully retracted position to the fully extended position; and/or the method may further include loading a balloon in the loading lumen and connecting the balloon to the handle to restrain motion of the balloon relative to the handle prior to moving the tube from the fully retracted position to the fully extended position; and/or the method may further include slotting a bridge into both the tube and the funnel during the step of axially aligning the first portion of the funnel with the distal end of the tube; and/or the step of disposing a prosthetic heart valve within the funnel may include folding the prosthetic heart valve to form a groove in the prosthetic heart valve complementary to a shape of the loading lumen and aligning the groove with the loading lumen.

Also disclosed is a heart valve delivery system including a handle having a longitudinally extending slot, a cavity, an annular adjustor with interior threading, and a pin block bounding an end of the cavity, the pin block includes a bore and a set screw extending into the bore; a shaft having a proximal end fixedly connected to the handle and extending distally along an axis away from the handle to a free end, the shaft having a shaft lumen extending from the proximal end to the distal end, and a retainer located at the free end and including an interior space in communication with the shaft lumen; a tube surrounding the shaft, the tube having a proximal end connected to the handle and extending distally along the axis away from the handle to a distal end and having a tube lumen extending from the proximal end of the tube to the distal end of the tube, the tube being axially movable relative to the shaft and the handle between a fully extended position at which the tube extends distally farther than the shaft, and a fully retracted position at which the shaft extends distally farther than the tube; a distal nose fixedly connected to the proximal end of the tube; an inserter having a tubular sheath with an inner diameter greater than an outer diameter of the tube, the inserter being releasably couplable to the distal nose to retrain axial movement of the inserter relative to the tube; and a funnel including a first portion having an inner diameter equal to an inner diameter of the tube, a second portion having an inner diameter greater than the inner diameter of the first portion, and a loading lumen extending from the first portion through the second portion.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A heart valve delivery system, comprising:
   a handle;
   a shaft having a proximal end fixedly connected to the handle and extending distally along an axis away from the handle to a free end;
   a tube surrounding the shaft, the tube having a proximal end connected to the handle and extending distally along the axis away from the handle to a distal end, the tube being axially movable relative to the shaft and the handle between a fully extended position at which the tube extends distally farther than the shaft, and a fully retracted position at which the shaft extends distally farther than the tube; and
   a funnel, the funnel including:
      a first portion having an inner diameter equal to an inner diameter of the tube;
      a second portion having an inner diameter greater than the inner diameter of the first portion; and
      a tapered loading space extending between the first portion and the second portion,
   wherein the funnel includes only a single protruding guide surface on the tapered loading space, the single protruding guide surface extending in a straight direction from the first portion to the second portion, the single protruding guide surface configured to prevent rotation of a prosthetic heart valve being loaded into the tube through the funnel.

2. The heart valve delivery system of claim 1, further comprising:
   a distal nose fixedly connected to the proximal end of the tube, the distal nose including a threaded shaft extending proximally into the handle; and
   an internally threaded adjustor ring rotatably connected to the handle and threadedly connected to the threaded shaft such that rotation of the adjustor ring relative to the handle axially moves the tube between the fully extended position and the fully retracted position.

3. The heart valve delivery system of claim 1, further comprising a retainer located at the free end of the shaft and having an interior space extending proximally from a distal end of the retainer.

4. The heart valve delivery system of claim 1, wherein a lumen extends continuously from the proximal end of the shaft to the free end of the shaft.

5. The heart valve delivery system of claim 4, further comprising:
   a pin block at a proximal end of the handle;
   a bore extending through the pin block; and
   a set screw selectively movable to impinge upon or clear the bore.

6. The heart valve delivery system of claim 1, further comprising:
   an inserter having a tubular sheath with an inner diameter greater than an outer diameter of the tube; and
   a distal nose fixedly connected to the proximal end of the tube, the distal nose being couplable to the inserter to restrain axial movement of the inserter relative to the tube.

7. The heart valve delivery system of claim 6, wherein the inserter includes a port near a proximal end of the inserter, the port being in communication with an interior of the sheath and extending transverse to the sheath.

8. The heart valve delivery system of claim 1, further comprising:
a storage lumen extending axially along the tube; and
the funnel including a loading lumen extending from the first portion through the second portion, the loading lumen being positioned within the single protruding guide surface.

9. The heart valve delivery system of claim 8, further comprising a bridge having a lumen extending therethrough, the lumen having a diameter at a first end equal to an inner diameter of the storage lumen and a diameter at another end equal to an inner diameter of the loading lumen.

10. The heart valve delivery system of claim 9, wherein the bridge includes laterally extending wings such that the bridge may align the loading lumen with the storage lumen and restrain rotation of the funnel about the axis relative to the tube.

11. A method of implanting a prosthetic heart valve into a patient's heart using the heart valve delivery system of claim 6, comprising:
inserting a distal end of the sheath into the heart; and
inserting a distal end of the tube into the sheath.

12. The method of claim 11, further comprising:
coupling the distal nose to the sheath; and
retracting the tube to the fully retracted position.

13. The method of claim 11, further comprising:
inflating a balloon disposed within the sheath such that part of the inflated balloon extends outward from the distal end of the sheath while advancing the sheath through the heart; and
deflating the balloon and removing the balloon from the sheath prior to inserting the distal end of the tube into the sheath.

14. The method of claim 11, further comprising:
loading the prosthetic heart valve into the tube before inserting the tube into the sheath.

15. The method of claim 14, wherein the step of loading the prosthetic heart valve includes securing an anchor of the prosthetic heart valve to the handle.

16. The method of claim 15, further comprising:
removing the sheath and the tube from the heart; and
tightening the anchor against an outside of the heart after removing the sheath and the tube from the heart.

17. A method of loading a prosthetic heart valve into the heart valve delivery system of claim 8, comprising:
axially aligning the first portion of the funnel with the distal end of the tube;
rotationally aligning the loading lumen of the funnel with the storage lumen along the tube;
disposing a prosthetic heart valve within the funnel and at a distal end of the shaft while the tube is in the fully retracted position;
securing an anchor of the prosthetic heart valve to the handle to restrain relative movement between the prosthetic heart valve and the handle, the prosthetic heart valve being connected to the anchor by a tether extending through the tube; and
extending the tube from the fully retracted position to the fully extended position.

18. The method of claim 17, further comprising loading a balloon in the loading lumen and connecting the balloon to the handle to restrain motion of the balloon relative to the handle prior to moving the tube from the fully retracted position to the fully extended position.

19. The method of claim 17, wherein the step of disposing the prosthetic heart valve within the funnel includes folding the prosthetic heart valve to form a groove in the prosthetic heart valve complementary to a shape of the loading lumen and aligning the groove with the loading lumen.

20. A heart valve delivery system, comprising:
a handle having a longitudinally extending slot, a cavity, an annular adjustor with interior threading, and a pin block bounding an end of the cavity, the pin block including a bore and a set screw extending into the bore;
a shaft having a proximal end fixedly connected to the handle and extending distally along an axis away from the handle to a free end, the shaft having a shaft lumen within the shaft from the proximal end to the distal end, and a retainer located at the free end and including an interior space in communication with the shaft lumen;
a tube surrounding the shaft, the tube having a proximal end connected to the handle and extending distally along the axis away from the handle to a distal end and having a tube lumen extending from the proximal end of the tube to the distal end of the tube, the tube being axially movable relative to the shaft and the handle between a fully extended position at which the tube extends distally farther than the shaft, and a fully retracted position at which the shaft extends distally farther than the tube;
a distal nose fixedly connected to the proximal end of the tube;
an inserter having a tubular sheath with an inner diameter greater than an outer diameter of the tube, the inserter being releasably couplable to the distal nose to restrain axial movement of the inserter relative to the tube; and
a funnel including a first portion having an inner diameter equal to an inner diameter of the tube, a second portion having an inner diameter greater than the inner diameter of the first portion, and a tapered loading space extending between the first portion and the second portion;
wherein the funnel includes only a single protruding guide surface on the tapered loading space, the single protruding guide surface extending in a straight direction from the first portion to the second portion, the single protruding guide surface configured to prevent rotation of a prosthetic heart valve being loaded into the tube through the funnel.

* * * * *